(12) United States Patent
Irving et al.

(10) Patent No.: US 12,403,275 B2
(45) Date of Patent: Sep. 2, 2025

(54) TARGETED FLUID EJECTION PROFILES

(71) Applicant: Rocket Science Health Corp., Victoria (CA)

(72) Inventors: Kenneth Irving, Victoria (CA); James Jackson, Victoria (CA); Timothy Rees, Victoria (CA); Manu Sharma, Victoria (CA)

(73) Assignee: Rocket Science Health Corp., Victoria (CA)

( * ) Notice: Subject to any disclaimer, the term of this patent is extended or adjusted under 35 U.S.C. 154(b) by 0 days.

(21) Appl. No.: 19/072,193

(22) Filed: Mar. 6, 2025

(65) Prior Publication Data
US 2025/0195801 A1    Jun. 19, 2025

Related U.S. Application Data

(63) Continuation of application No. PCT/IB2024/057747, filed on Aug. 9, 2024.

(60) Provisional application No. 63/518,384, filed on Aug. 9, 2023, provisional application No. 63/518,389, filed on Aug. 9, 2023.

(51) Int. Cl.
    *A61M 15/08* (2006.01)

(52) U.S. Cl.
    CPC .................. *A61M 15/08* (2013.01)

(58) Field of Classification Search
    CPC .... A61M 15/08; A61M 31/00; A61M 31/002; A61M 2210/0618
    See application file for complete search history.

(56) References Cited

U.S. PATENT DOCUMENTS

| 11,278,709 | B1* | 3/2022 | Mathai | A61K 31/485 |
| 2019/0015613 | A1* | 1/2019 | Shahaf | A61M 15/0035 |
| 2020/0353183 | A1* | 11/2020 | Alt | A61M 15/08 |
| 2021/0316088 | A1* | 10/2021 | Shahaf | A61M 15/0031 |

FOREIGN PATENT DOCUMENTS

WO    2025032552 A2    2/2025

OTHER PUBLICATIONS

Written Opinion Issued in PCT Application No. PCT/IB24/57747, mailed on Jan. 13, 2025, 6 Pages.

* cited by examiner

*Primary Examiner* — Dung T Ulsh
(74) *Attorney, Agent, or Firm* — Mintz, Levin, Cohn, Ferris, Glovsky and Popeo, P.C.

(57) ABSTRACT

Provided herein are methods of delivering a low viscosity fluid to a targeted sub-region of a subject's nasal cavity via delivery as a continuous liquid stream.

20 Claims, 18 Drawing Sheets

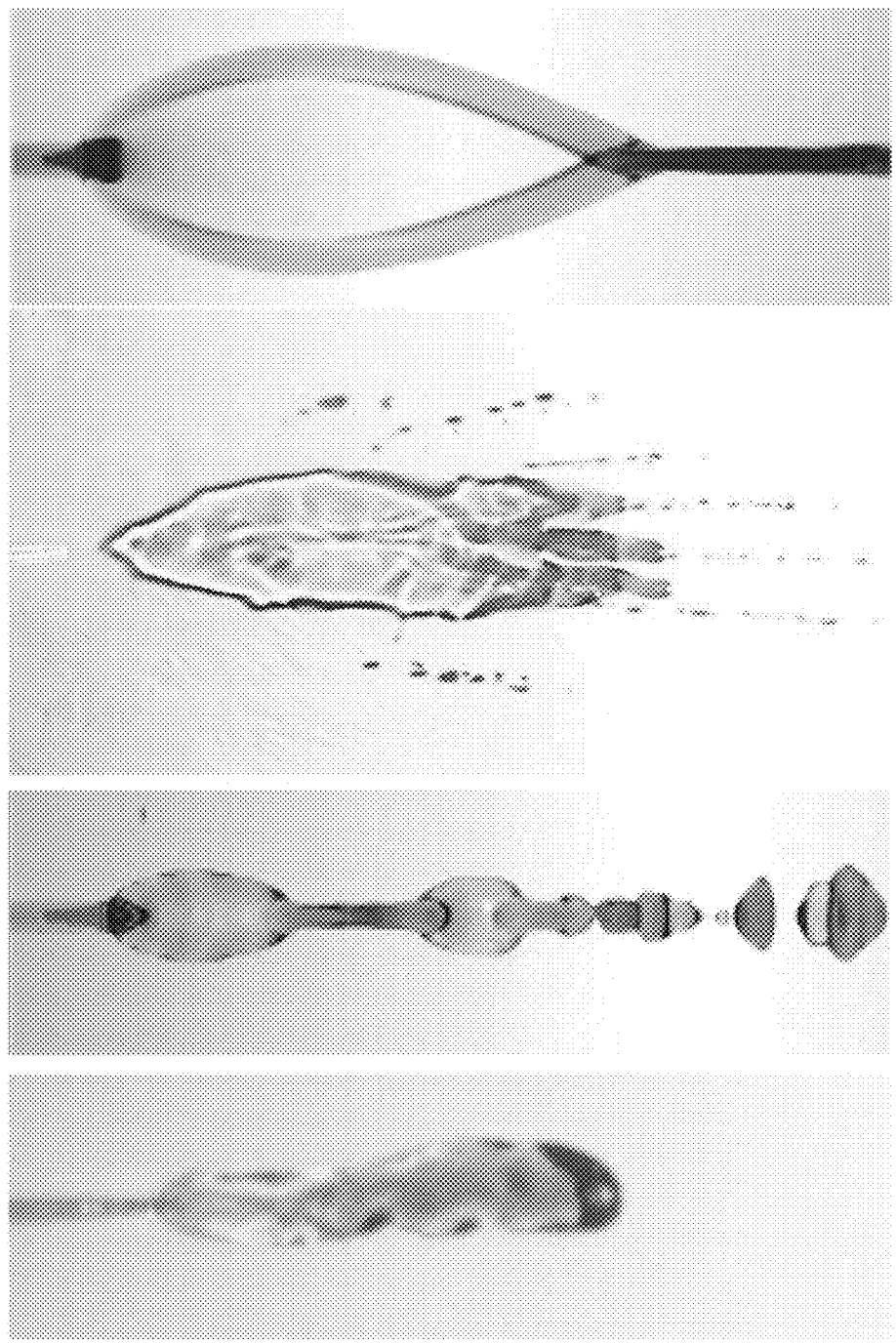

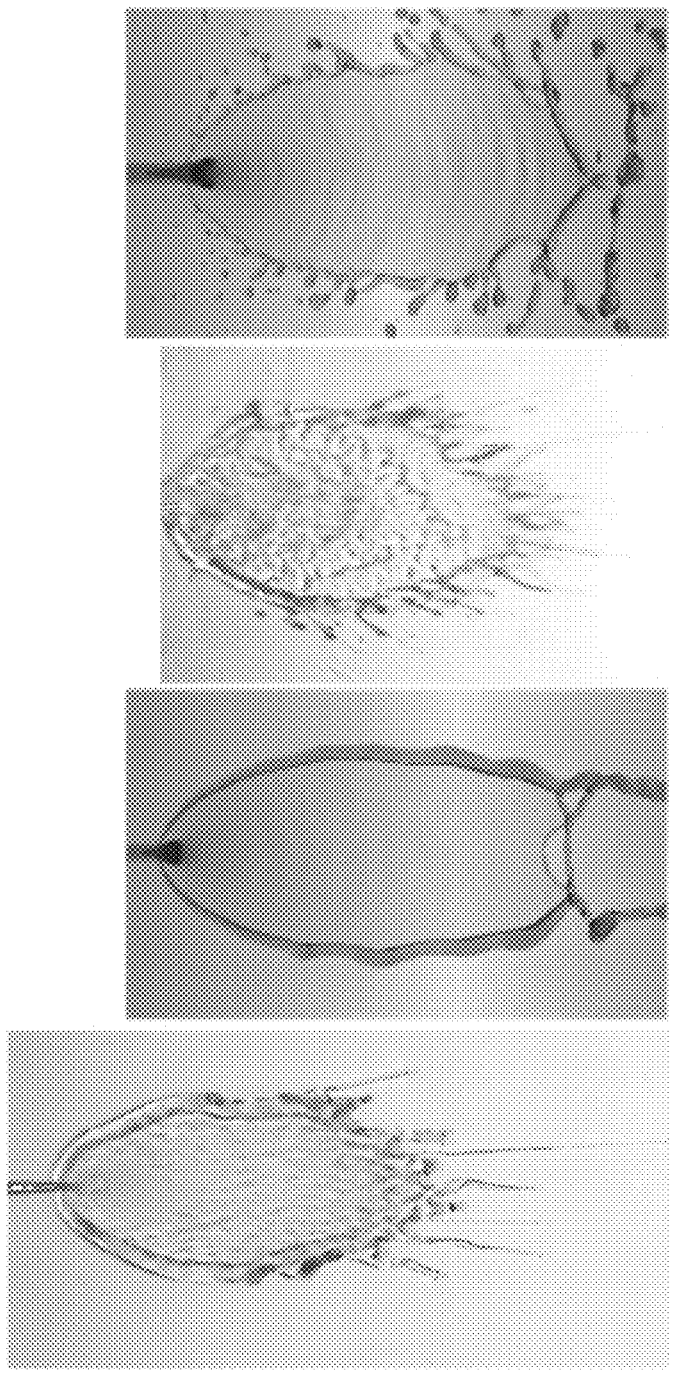

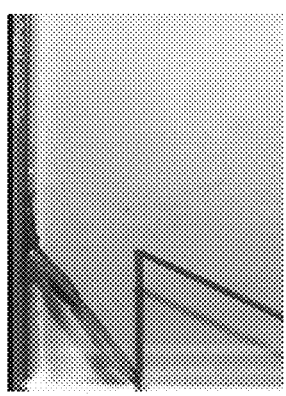
FIG. 15A
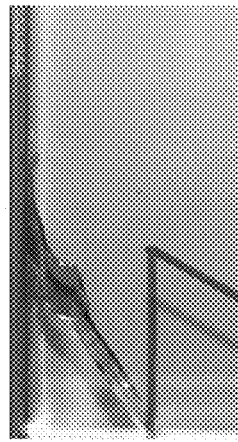
FIG. 15B
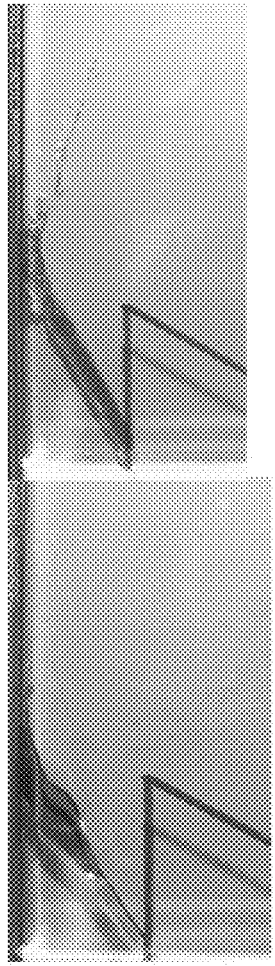
FIG. 15C
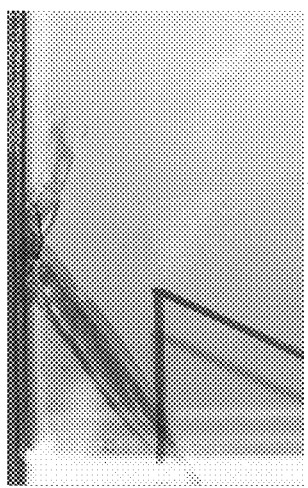
FIG. 15D
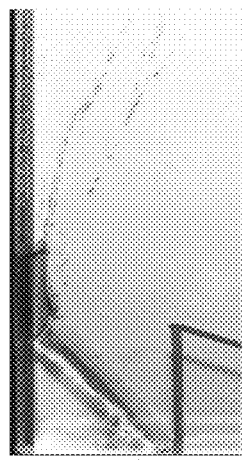
FIG. 15E
FIG. 15F
FIG. 15G
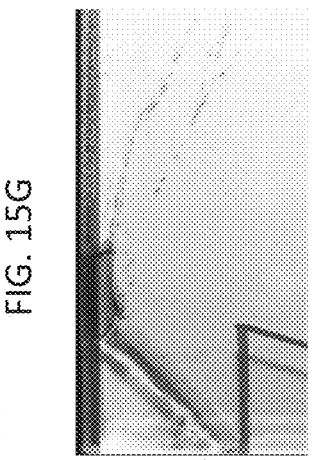
FIG. 15H
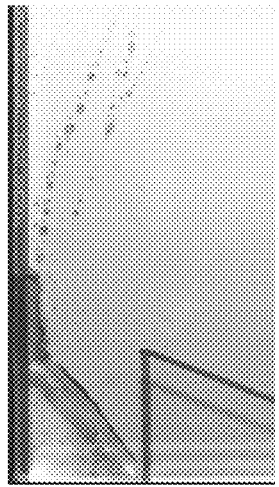
FIG. 15I

TARGETED FLUID EJECTION PROFILES

CROSS REFERENCE

This application is a continuation of International Patent Application No. PCT/IB24/057747, filed Aug. 9, 2024, which claims the benefit of priority to U.S. Provisional Application No. 63/518,384, filed Aug. 9, 2023, and U.S. Provisional Application No. 63/518,389, filed Aug. 9, 2023, the contents of which are incorporated herein by reference in its entirety, including any drawings.

BACKGROUND

Intranasal drug delivery is an effective route for the administration of certain medications, for example, those that act locally in the nasal channel, or those that are rapidly absorbed into the bloodstream through the nasal mucosa. Among the challenges associated with delivering compositions to the nasal channel of a subject includes difficulty in accommodating for variations in nasal channel, targeting deposition of the therapeutic compound at the correct location in the nasal channel, and repeatably delivering a composition to on-target locations within the nasal channel with a high degree of precision across a population of subjects.

SUMMARY

It is appreciated by the inventors that current methods of delivering intranasal drugs to the nasal cavity fail to provide for on-target delivery of drugs to specific sub-regions of the nasal cavity, and have a high propensity for off-target delivery. Many intranasal delivery methods focus heavily on maximizing coating of the mucosal surface of the nasal cavity as to maximize mass transfer across the mucosa and into blood stream. However, there exists opportunity for delivering drugs to particular organ systems by targeted delivery of a fluid comprising the drug to specific sub-regions of the nasal cavity, for example, delivering a drug to the cerebral spinal fluid (CSF), central nervous system (CNS), and brain by targeting delivery of the drug to the olfactory cleft. Certain classes of drugs when administered intranasally are preferably absorbed in particular subregions of the nasal cavity, or are only active in particular subregions of the nasal cavity with certain cell types, and increasing on-target delivery of fluids to the correct subregion of the nasal cavity while minimizing off-target delivery can provide for new routes of drug administration, improved therapeutic response, reduced side effects, improved therapeutic safety profiles, and reduced effective doses. Further, certain classes of drugs, especially large molecule drugs, comprise very delicate active agents which are not suitable for traditional intranasal delivery methods, such as sprays, that introduce significant shear stress to the fluid, and risk damaging the therapeutic molecule. Accordingly, disclosed herein are methods for delivering fluids to targeted subregions of the nasal cavity, which maximize on-target delivery, and minimize off target delivery. Such methods may be suitable for the targeted delivery of a fluid to the olfactory cleft, or the delivery of large molecule drugs in a manner which does not risk damaging the therapeutic molecule. The methods may also be suitable for the targeted delivery of low viscosity fluids which are difficult to direct to targeted subregions, while not directing the fluid to off-target subregions.

In one aspect, disclosed herein is a method of delivering a fluid having a viscosity of less than about 3000 centipoise (cP) to a targeted sub-region of a subject's nasal cavity, the method comprising: a) ejecting a discrete volume of the fluid as a continuous stream from a dispensing element of a device; b) moving the continuous stream through an airspace in the nasal cavity towards the targeted sub-region; c) contacting an anatomical feature of the subject's nasal cavity with the continuous stream and forcing the fluid to move around the anatomical feature and towards the targeted sub-region; and d) contacting the targeted sub-region of the subject's nasal cavity with the fluid, thereby delivering the fluid to the targeted sub-region of the subject's nasal cavity. In some embodiments, the viscosity of the fluid is less than about 2500 cP. In some embodiments, the viscosity of the fluid is less than about 2000 cP. In some embodiments, the viscosity of the fluid is less than about 1500 cP. In some embodiments, the viscosity of the fluid is less than about 1000 cP. In some embodiments, the viscosity of the fluid is less than about 500 cP. In some embodiments, the viscosity of the fluid is less than about 250 cP. In some embodiments, the viscosity of the fluid is less than about 100 cP. In some embodiments, the viscosity of the fluid is less than about 50 cP. In some embodiments, at a distance of 5 mm from the dispensing tip, a flux through a planar surface orthogonal to a flow path of the continuous stream possesses a gas component by volume not exceeding about 35%. In some embodiments, the gas component does not exceed about 20% by volume. In some embodiments, the ejecting the continuous stream of the fluid from the dispensing element results in a change in a velocity of the fluid of less than about 25%, when measured from a first point before ejection from the dispensing element to a second point 5 mm after ejection from the dispensing element, and wherein optionally, the first point before ejection from the dispensing element is within the dispensing element up to 3 mm from the point of ejection. In some embodiments, the change in the velocity of the fluid is less than about 10%. In some embodiments, the method does not result in substantial deposition of the fluid in a region of the subject's nasal cavity, which is not the targeted sub-region, immediately following the contacting of step (d). In some embodiments, the method results in less than about 10% of the fluid being deposited in a region of the subject's nasal cavity, which is not the targeted sub-region, immediately following the contacting of step (d). In some embodiments, forcing the fluid to move around the anatomical feature comprises changing a direction of movement of the fluid relative to a direction of movement of the fluid in (b). In some embodiments, at a distance of 1 mm from the dispensing tip, a flux through a planar surface orthogonal to a flow path of the continuous stream possesses a gas component not exceeding about 20% vol. In some embodiments, at a distance of 5 mm from the dispensing tip, the flux through a planar surface orthogonal to a flow path of the continuous stream possesses a gas component not exceeding about 10% vol. In some embodiments, at a distance of 5 mm from the dispensing tip, the flux through a planar surface orthogonal to a flow path of the continuous stream possesses a gas component not exceeding about 5% vol. In some embodiments, at a distance of 5 mm from the dispensing tip, the flux through a planar surface orthogonal to a flow path of the continuous stream possesses a gas component not exceeding about 1% vol. In some embodiments, the ejecting the continuous stream of the fluid from the dispensing elements change a velocity of the fluid by less than about 5%. In some embodiments, wherein the ejecting the discrete volume of the fluid as the continuous stream ejects the continuous stream in a velocity vector of the continuous stream which has a vorticity of less than about 0.2× the magnitude of the velocity vector at the time of the ejecting from the dispensing element. In some embodiments, the moving the continuous stream through the airspace in the nasal cavity occurs along a velocity vector of the continuous stream which has a vorticity of less than about 0.2× the magnitude of the velocity vector at the time of the ejecting from the dispensing element. In some embodiments, the continuous stream is ejected in a non-rotating vector. In some embodiments, the contacting the targeted sub-region of the subject's nasal cavity comprises depositing the fluid onto the targeted sub-region in a bolus deposition pattern, immediately following the contacting of step (d). In some embodiments, the bolus deposition pattern comprises deposition of the continuous stream onto the targeted sub-region in a cohesive liquid mass. In some embodiments, the cohesive liquid mass comprises at least about 75% of the fluid ejected from the dispensing element. In some embodiments, the bolus deposition pattern comprises deposition of the continuous stream onto the targeted sub-region without substantial formation of droplets, immediately following the contacting of step (d). In some embodiments, less than about 15% of the fluid ejected from the dispensing element forms droplets. In some embodiments, ejecting the continuous stream of the fluid from the dispensing element occurs at a velocity of about 1.5 m/s to about 3 m/s. In some embodiments, the viscosity of the fluid is about 1 cP. In some embodiments, the viscosity of the fluid is about 1 cP to about 10 cP. In some embodiments, the ejecting the continuous stream of the fluid from the dispensing element occurs at a velocity of up to about 20 m/s. In some embodiments, the ejecting the continuous stream of the fluid from the dispensing element occurs at a velocity of about 5 m/s to about 15 m/s. In some embodiments, the viscosity of the fluid is at least about 10 cP. In some embodiments, the viscosity of the fluid is about 10 cP to about 100 cP. In some embodiments, the viscosity of the fluid is about 25 cP to about 75 cP. In some embodiments, the viscosity of the fluid is about 50 cP. In some embodiments, ejecting the continuous stream of the fluid from the dispensing element results in the formation of a liquid chain fluid profile or a semi-closed rim fluid profile upon the contacting of step (c). In some embodiments, the contacting the targeted sub-region of the subject's nasal cavity comprises depositing the fluid onto the targeted sub-region in a surface deposition pattern, immediately following the contacting of step (d). In some embodiments, the surface deposition pattern comprises deposition of the continuous stream onto the targeted sub-region in a liquid sheet. In some embodiments, the liquid sheet comprises substantially no droplets. In some embodiments, the liquid sheet comprises less than about 10% of the fluid ejected forming droplets. In some embodiments, the droplets comprise a diameter of about 120 micrometers to about 0.5 millimeters. In some embodiments, the surface deposition pattern comprises deposition of the continuous stream onto the targeted sub-region in a plurality of droplets with a diameter of more than about 120 micrometers. In some embodiments, the ejecting the continuous stream of the fluid from the dispensing element occurs at a velocity of about 3 m/s to about 11 m/s. In some embodiments, the ejecting the continuous stream of the fluid from the dispensing element occurs at a velocity of about 7 m/s to about 11 m/s. In some embodiments, the viscosity of the fluid is about 1 cP. In some embodiments, the viscosity of the fluid is about 1 cP to about 10 cP. In some embodiments, ejecting the continuous stream of the fluid from the dispensing element results in the formation of a liquid rim fluid profile upon the contacting of step (c). In some embodiments, the liquid rim fluid profile comprises a semi-closed rim fluid profile, an open rim fluid profile, or an unstable rim fluid profile. In some embodiments, the contacting the targeted sub-region of the subject's nasal cavity comprises depositing the fluid onto the targeted sub-region in a droplet deposition pattern, immediately following the contacting of step (d). In some embodiments, the droplet deposition pattern comprises deposition of the continuous stream onto the targeted sub-region in a plurality of droplets with a diameter of about 120 micrometers to about 0.5 millimeters. In some embodiments, the ejecting the continuous stream of the fluid from the dispensing element occurs at a velocity of at least about 11 m/s. In some embodiments, the viscosity of the fluid is about 1 cP. In some embodiments, the viscosity of the fluid is about 1 cP to about 10 cP. In some embodiments, ejecting the continuous stream of the fluid from the dispensing element results in the formation of an impact wave fluid profile upon the contacting of step (c). In some embodiments, the targeted sub-region is an olfactory cleft. In some embodiments, the contacting the olfactory cleft comprises coating a surface of the olfactory cleft. In some embodiments, the contacting the olfactory cleft comprises partially filling a volume of the nasal cavity comprising the olfactory cleft. In some embodiments, a capillary bridge is formed by the fluid, wherein the capillary bridge contacts opposing sides of an olfactory region of the subject's nasal cavity and supports a coating of the fluid about the olfactory cleft. In some embodiments, the targeted sub-region is an olfactory cleft. In some embodiments, the targeted sub-region is a middle turbinate. In some embodiments, the contacting the middle turbinate comprises coating a surface of the middle turbinate. In some embodiments, the contacting the middle turbinate partially filling a volume of the nasal cavity comprising the middle turbinate. In some embodiments, the targeted sub-region is a middle turbinate. In some embodiments, moving the continuous stream through the airspace in the nasal cavity comprises the continuous stream traveling at least about 0.2 cm through the airspace before contacting the targeted subregion. In some embodiments, the targeted subregion is an olfactory cleft of the subject, and wherein substantially none of the fluid is deposited outside of the olfactory cleft of the subject, immediately following the contacting of step (d). In some embodiments, the targeted subregion is an olfactory cleft of the subject, and wherein less than about 10% vol. of the fluid is deposited outside of the olfactory cleft of the subject, immediately following the contacting of step (d). In some embodiments, the targeted subregion is a middle turbinate of the subject, and wherein substantially none of the fluid is deposited outside the middle turbinate of the subject, immediately following the contacting of step (d). In some embodiments, the targeted subregion is a middle turbinate of the subject, and wherein less than about 10% of the fluid is deposited outside the middle turbinate of the subject, immediately following the contacting of step (d). In some embodiments, the ejecting the bolus of the fluid from the dispensing element occurs with a Reynolds number of less than about 2,000 measured at the point of ejection from the dispensing element. In some embodiments, the ejecting the bolus of the fluid from the dispensing element occurs with a Reynolds number of less than about 500 measured at the point of ejection from the dispensing element. In some embodiments, the discrete volume of the fluid comprises a volume of up to about 200 µL. In some embodiments, the discrete volume of the fluid comprises a volume is about 100 µL. In some embodiments, the discrete volume of the fluid comprises a volume of about 50 µL to about 200 µL. In some embodiments, the dispensing element comprises an unobstructed opening at the tip of the dispensing element. In some embodiments, the dispensing element does not comprise an atomizer. In some embodiments, the feature of the nasal cavity is a septum. In some embodiments, a diameter of the continuous stream is about 1 mm to about 10 mm upon the ejecting from the dispensing element. In some embodiments, a diameter of the continuous stream is about 0.3 mm to about 6 mm the ejecting from the dispensing element. In some embodiments, the fluid comprises a medicament. In some embodiments, the medicament comprises a biologic, a protein, a nucleic acid, a vaccine, or a large molecule drug. In some embodiments, the medicament comprises a small molecule drug. In some embodiments, the ejecting of the discrete volume of the fluid occurs at a velocity of up to 50 m/s.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 9A shows an exemplary image of liquid chain fluid formation, per one or more embodiments herein;

FIG. 9B shows an exemplary image of liquid chain fluid formation, per one or more embodiments herein;

FIG. 9C shows an exemplary image of semi-closed rim fluid formation, per one or more embodiments herein;

FIG. 9D shows an exemplary image of closed rim fluid formation, per one or more embodiments herein;

FIG. 10A shows an exemplary image of an open rim fluid formation, per one or more embodiments herein;

FIG. 10B shows an exemplary image of an open rim fluid formation, per one or more embodiments herein;

FIG. 10C shows an exemplary image of an unstable rim fluid formation, per one or more embodiments herein;

FIG. 10D shows an exemplary image of an unstable rim fluid formation, per one or more embodiments herein;

FIG. 15A illustrates an initial state of a high viscosity fluid upon striking a curved glass sheet and failing to form a bolus deposition pattern, per one or more embodiments herein;

FIG. 15B illustrates a high viscosity in an intermediate state of a fluid after striking a curved glass sheet following impact and prior to failing to form a bolus deposition pattern, per one or more embodiments herein;

FIG. 15C illustrates a final state of a high viscosity fluid after striking a curved glass sheet and coming to rest and failing to form a bolus deposition pattern, per one or more embodiments herein;

FIG. 15D illustrates an initial state of a high viscosity fluid upon striking a curved glass sheet and prior to forming a bolus deposition pattern per one or more embodiments herein;

FIG. 15E illustrates an intermediate state of a high viscosity fluid after striking a curved glass sheet following impact and prior to forming a bolus deposition pattern, per one or more embodiments herein;

FIG. 15F illustrates a final state of a high viscosity fluid after striking a curved glass sheet and coming to rest and forming a bolus deposition pattern, per one or more embodiments herein;

FIG. 15G illustrates an initial state of a high viscosity fluid upon striking a curved glass sheet and prior to forming a bolus deposition pattern, per one or more embodiments herein;

FIG. 15H illustrates an intermediate state of a high viscosity fluid after striking a curved glass sheet following impact and prior to forming a bolus deposition pattern, per one or more embodiments herein;

FIG. 15I a final state of a high viscosity fluid after striking a curved glass sheet and coming to rest and forming a bolus deposition pattern, per one or more embodiments herein;

DETAILED DESCRIPTION

Figure 1:
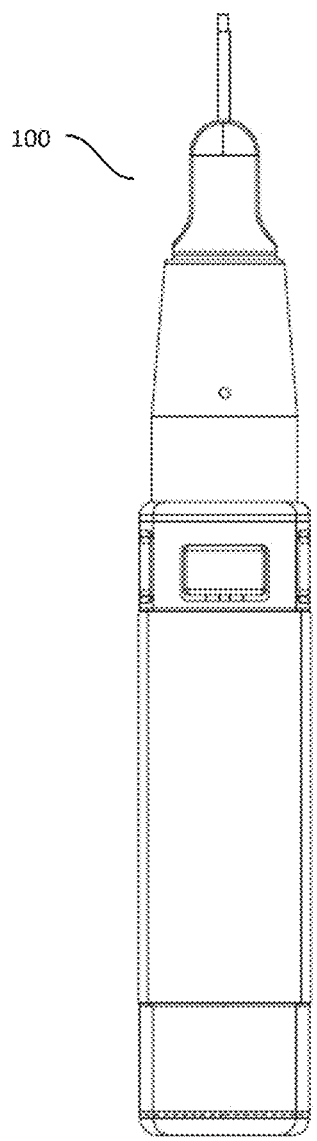
FIG. 1 depicts an exemplary ejection device, per one or more embodiments herein.

It is appreciated by the inventors that current methods of delivering intranasal drugs to the nasal cavity fail to provide for on-target delivery of drugs to specific sub-regions of the nasal cavity, and have a high propensity for off-target delivery. Many intranasal delivery methods focus heavily on maximizing coating of the mucosal surface of the nasal cavity as to maximize mass transfer across the mucosa and into blood stream. However, there exists opportunity for delivering drugs to particular organ systems by targeted delivery of a fluid comprising the drug to specific sub-regions of the nasal cavity, for example, delivering a drug to the cerebral spinal fluid (CSF), central nervous system (CNS), and brain by targeting delivery of the drug to the olfactory cleft. Certain classes of drugs when administered intranasally are preferably absorbed in particular subregions of the nasal cavity, or are only active in particular subregions of the nasal cavity with certain cell types, and increasing on-target delivery of fluids to the correct subregion of the nasal cavity while minimizing off-target delivery can provide for new routes of drug administration, improved therapeutic response, reduced side effects, improved therapeutic safety profiles, and reduced effective doses. Further, certain classes of drugs, especially large molecule drugs, comprise very delicate active agents which are not suitable for traditional intranasal delivery methods, such as sprays, that introduce significant shear stress to the fluid, and risk damaging the therapeutic molecule. Accordingly, disclosed herein are methods for delivering fluids to targeted subregions of the nasal cavity, which maximize on-target delivery, and minimize off target delivery. Such methods may be suitable for the targeted delivery of a fluid to the olfactory cleft, or the delivery of large molecule drugs in a manner which does not risk damaging the therapeutic molecule. The methods may also be suitable for the targeted delivery of low viscosity fluids and mid-viscosity fluids which are difficult to direct to targeted subregions of the nasal cavity.

In one aspect, disclosed herein is a method of delivering a fluid having a viscosity of less than about 3000 centipoise (cP) to a targeted sub-region of a subject's nasal cavity, the method comprising: a) ejecting a discrete volume of the fluid as a continuous stream from a dispensing element of a device; b) moving the continuous stream through an airspace in the nasal cavity towards the targeted sub-region; c) contacting an anatomical feature of the subject's nasal cavity with the continuous stream and forcing the fluid to move around the anatomical feature and towards the targeted sub-region; and d) contacting the targeted sub-region of the subject's nasal cavity with the fluid, thereby delivering the fluid to the targeted sub-region of the subject's nasal cavity. The methods disclosed herein can permit for targeted deposition of a fluid to a subregion of the nasal cavity, and can prevent or minimize off-target deposition of the fluid to non-targeted regions of the nasal cavity. In some embodiments, the targeted region may comprise the olfactory cleft. In some embodiments, the targeted region may comprise the upper respiratory system. In some embodiments, the targeted region may comprise the middle turbinate. In some embodiments, the targeted region may comprise the superior turbinate.

Nasal Anatomy

The methods of the present disclosure may comprise ejecting a discrete volume of a fluid as a continuous liquid stream from dispensing element to target a particular subregion of a nasal cavity, such as one or both olfactory clefts, one or both middle meatuses, one or both middle turbinates, one or both superior turbinates, or the upper respiratory system. Such methods disclosed herein permit for the highly targeted delivery of drugs to the subregions of the nasal cavity, and can prevent or minimize off-target deposition of the fluid to non-targeted regions of the nasal cavity.

Figure 2A:
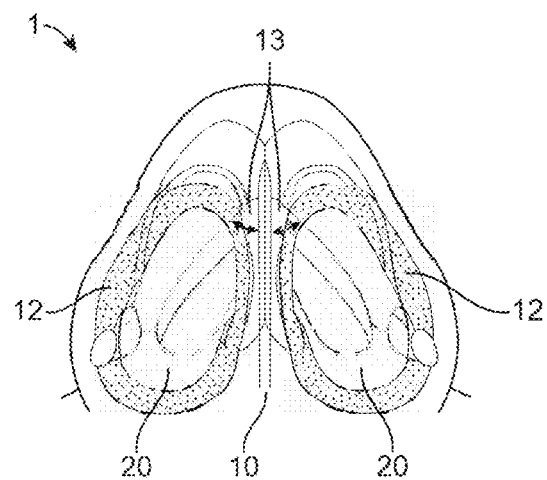
FIG. 2A depicts a bottom view of an exemplary embodiment of a subject's nose.
Figure 2B:
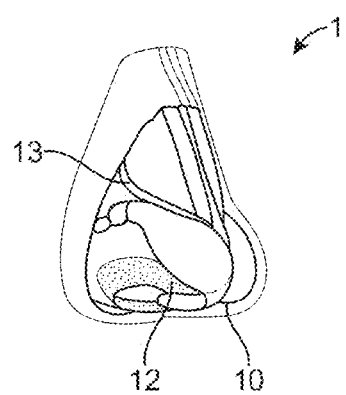
FIG. 2B depicts a side view of an exemplary embodiment of a subject's nose.

FIG. 2A depicts a bottom view of an exemplary embodiment of a subject's nose. FIG. 2B depicts a side view of an exemplary embodiment of a subject's nose. In some embodiment's the nose 1 has a columella region 10 between the entrance to two nasal channels 20. In some embodiments, the nose 1 has an external nasal valve 12 coupled to the nasal channel 20. In some embodiments, the nose 1 has an internal nasal valve 13 (INV) coupled to the nasal channel 20. As is shown in FIGS. 2A-2B, there are a number of soft tissue structures which can obstruct the nasal channel and prevent the movement of a continuous liquid stream through the nasal cavity. The INV 13 may act as a barrier to effective delivery of a fluid to a targeted subregion of the nasal cavity, obstructing fluid from moving past the INV, and stopping the movement of a fluid through the nasal cavity. In some embodiments, the continuous liquid stream is ejected from above the INV. In some embodiments, the continuous liquid stream is ejected from a position superior the INV.

Figure 3A:
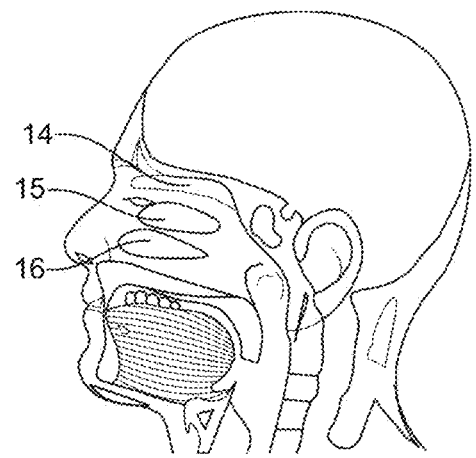
FIG. 3A depicts a side view of a representation subject's nasal channel.
Figure 3B:
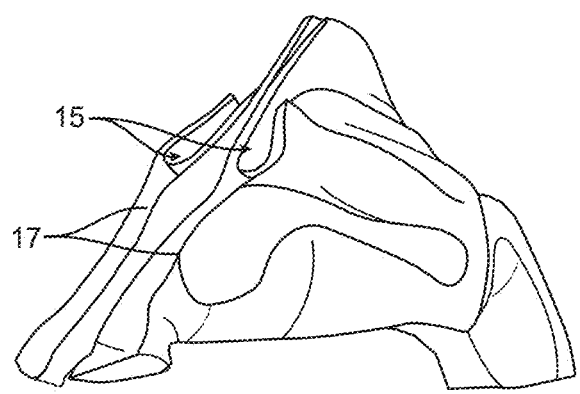
FIG. 3B depicts a side view of an exemplary embodiment of a representation subject's nasal channels from the vestibule to the olfactory cleft based on a posteriorly oriented plane.
Figure 4A:
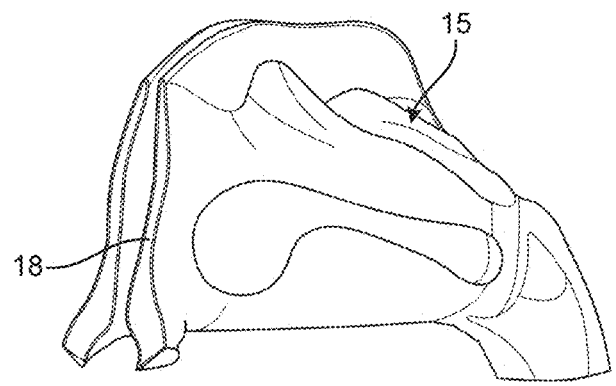
FIG. 4A depicts a side view of an exemplary embodiment of a representation subject's nasal channels from the vestibule to the olfactory cleft based on an anteriorly oriented plane.
Figure 4B:
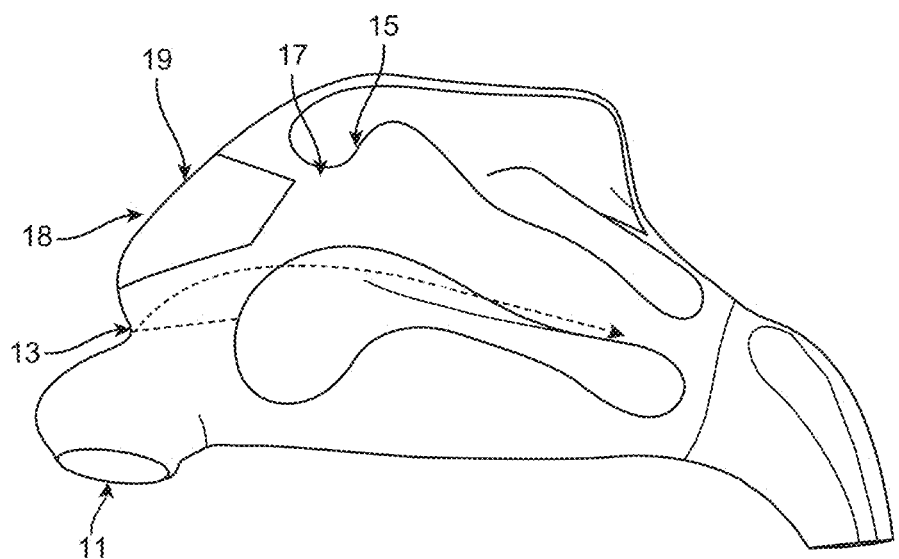
FIG. 4B depicts a side view of an exemplary embodiment of a representation a target ejection zone, according to some embodiments.
Figure 5:
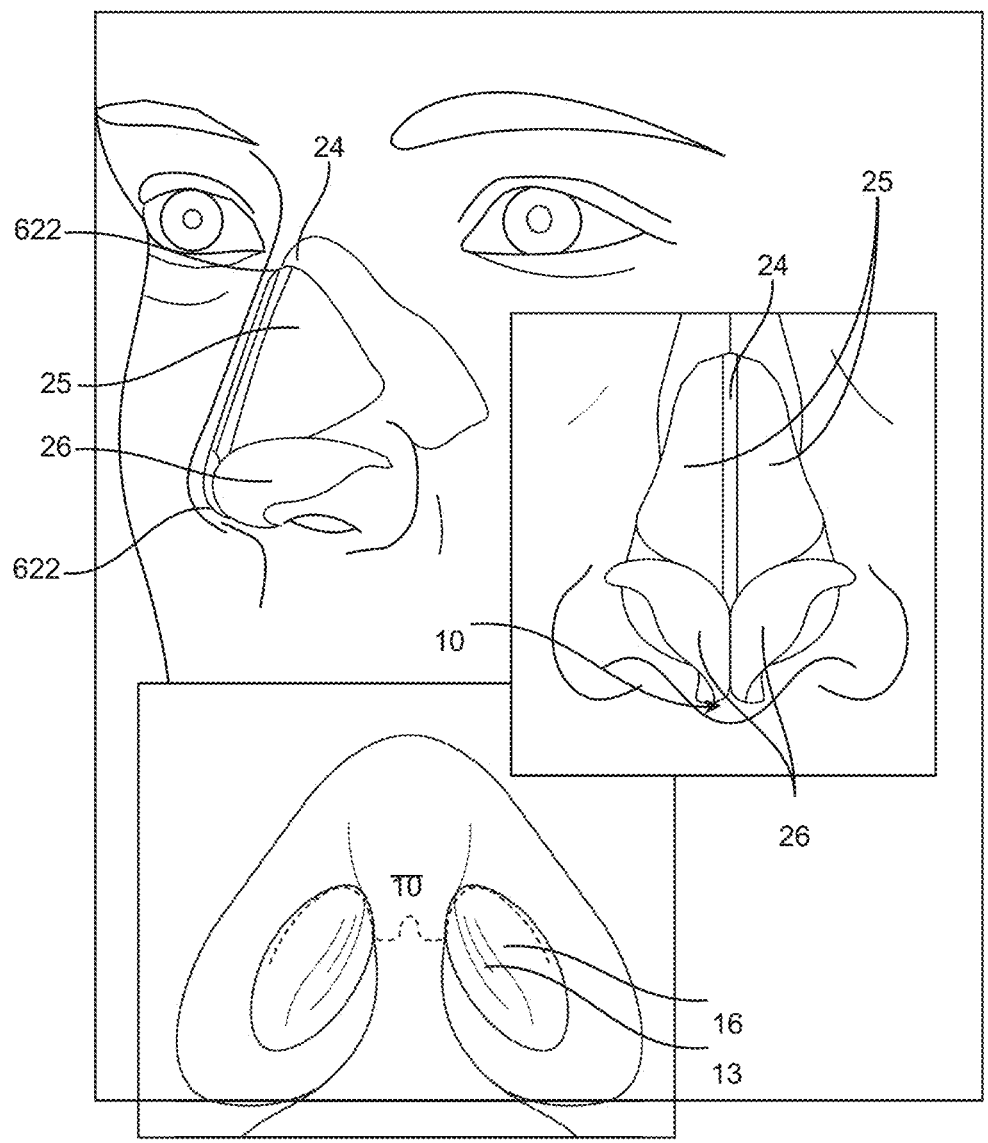
FIG. 5 depicts a front, base and perspective view of an exemplary embodiment of a subject's nose and the columella region.

FIG. 3A depicts a side view of an exemplary embodiment of a subject's nasal cavity showing an inferior turbinate 16, a middle turbinate 15, and a superior turbinate 14. In some embodiments, the continuous liquid stream is ejected with a velocity having a trajectory which directed to the middle turbinate. In some embodiments, the continuous liquid stream is primarily deposited in the middle turbinate, and is not deposited in a superior turbinate or inferior turbinate. In some embodiments, the continuous liquid stream is ejected with a velocity having a trajectory which directed to the superior turbinate. In some embodiments, the continuous liquid stream is primarily deposited in the superior turbinate, and is not deposited in a middle turbinate or inferior turbinate. FIG. 3B depicts an angled side view of an exemplary embodiment of a representation subject's nasal channels 20 from the vestibules 21 to the olfactory clefts based on a posteriorly oriented plane 17 showing the middle turbinates 15. As is shown in FIG. 3B, the pathway from the nasal channel to the middle and superior turbinate are relatively narrow. In some cases, targeting delivery of a fluid to the middle or superior turbinate may comprise ejecting the continuous liquid stream from the nasal channel and into the middle or superior turbinate without substantially contacting other regions the nasal cavity with the fluid. FIG. 4A depicts an angled side view of an exemplary embodiment of a representation subject's nasal channels 20 from the vestibules to the olfactory clefts based on an anteriorly oriented plane 18. As is shown in FIG. 4A, the pathway from the nasal channel to the olfactory cleft is small and narrow, and preferentially targeting the olfactory cleft is difficult due to the small accessible area of the nasal cavity, and its close proximity to the superior and/or middle turbinate. In some cases, targeting delivery of a fluid to the olfactory cleft may comprise ejecting the continuous liquid stream from the nasal channel along a trajectory which is directed to the olfactory cleft and which does not substantially contact other regions the nasal cavity with the fluid, such as the superior turbinate or the middle turbinate. FIG. 4B depicts a side view of an exemplary embodiment of a representation subject's target ejection area 19. In some embodiments, the ejecting the continuous stream of fluid occurs from the target ejection zone as specified in FIG. 4B. In some embodiments, the ejecting the continuous stream of fluid from the target ejection zone enables the targeting of the olfactory cleft. In some embodiments, the ejecting the continuous stream of fluid from the target ejection zone enables the targeting of the middle turbinate. In some embodiments, the ejecting the continuous stream of fluid from the target ejection zone enables the targeting of the superior turbinate. FIG. 5 depicts a front, base and perspective view of an exemplary embodiment of a representation subject's nose exposing the columella region 10. The respiratory regions comprise turbinates that present physical obstacles (e.g., INV) to delivery to the upper reaches of a nasal channels 20, e.g., the olfactory clefts 23. Each respiratory region comprises at least one superior turbinate 14. Each respiratory region comprises at least one middle turbinate 15. Each respiratory region comprises at least one inferior turbinate 16. Each respiratory region comprises at least one posterior pathway 17 that involves at least one middle turbinate 15. Each respiratory region comprises at least one anterior pathway 18 that does not involve at least one middle turbinate 15.

In some cases, the middle turbinate 15 comprises a physical obstruction (e.g., INV, deviated septum, swollen nasal tissue, etc.) for composition delivery to an olfactory cleft. In some cases, the middle turbinate 15 comprises a most anterior aspect about aligned with the check bone. In some embodiments, the middle turbinate 15 comprises a most anterior aspect not aligned with the check bone. In some cases, the nasal channels 20 simplify anteriorly, and comprise angled pathways without one or more turbinates presenting physical obstacles to delivering a composition 111 to the upper nasal channels, including the olfactory clefts 23, or directing compositions 111 down one or more meatuses, e.g., the middle meatus 30, to the nasopharynx. In some cases, the nasal channel 20 comprises one pathway from the vestibule 21 to the olfactory cleft 23 based on an anteriorly oriented plane 18 with a target ejection point 19. In some embodiments, the nose comprises the nasal septum 24, upper lateral cartilage 25, and lower lateral cartilage 26.

Figure 6:
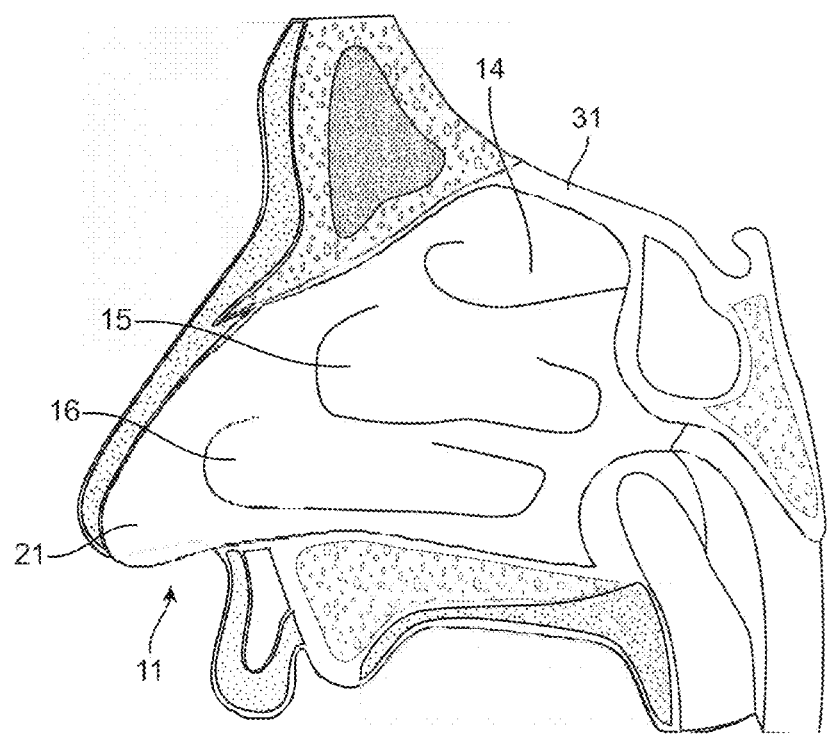
FIG. 6 depicts a side view of an exemplary embodiment of a representation subject's nasal cavity, including internal anatomical features.

FIG. 6 depicts a side view of an exemplary embodiment of a representation subject's nasal cavity. In some cases, the subject's nasal cavity 11 comprises the nasal vestibule 21, inferior turbinate 16, middle turbinate 15, superior turbinate 14, cribriform plate 31 or a combination thereof. In some embodiments, the targeted subregion of the nasal cavity comprise the middle turbinate 15, superior turbinate 14, cribriform plate 31, or olfactory cleft. In some embodiments, targeted deposition of the fluid to the middle turbinate 15, superior turbinate 14, cribriform plate 31, or olfactory cleft is achieved by ejection of a continuous liquid stream to the middle turbinate 15, superior turbinate 14, cribriform plate 31, or olfactory cleft, along a trajectory which does not result in the fluid contacting off-target regions the nasal cavity.

Figure 7A:
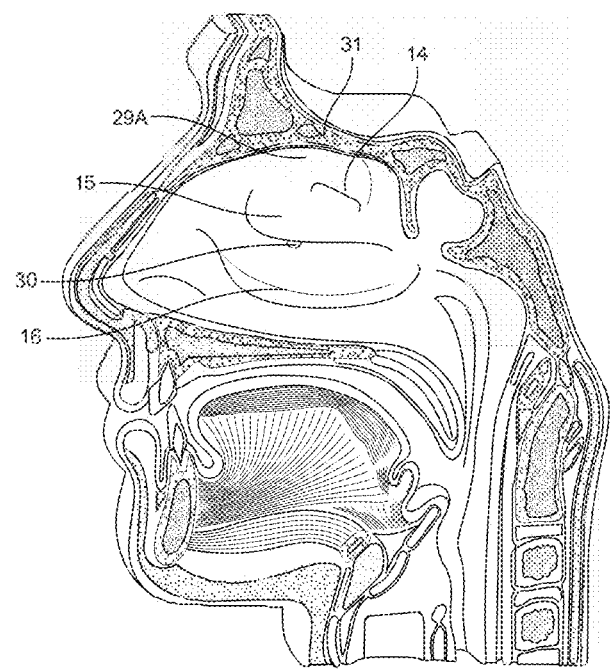
FIG. 7A depicts a side view of an exemplary embodiment of a representation subject's sinus.
Figure 7B:
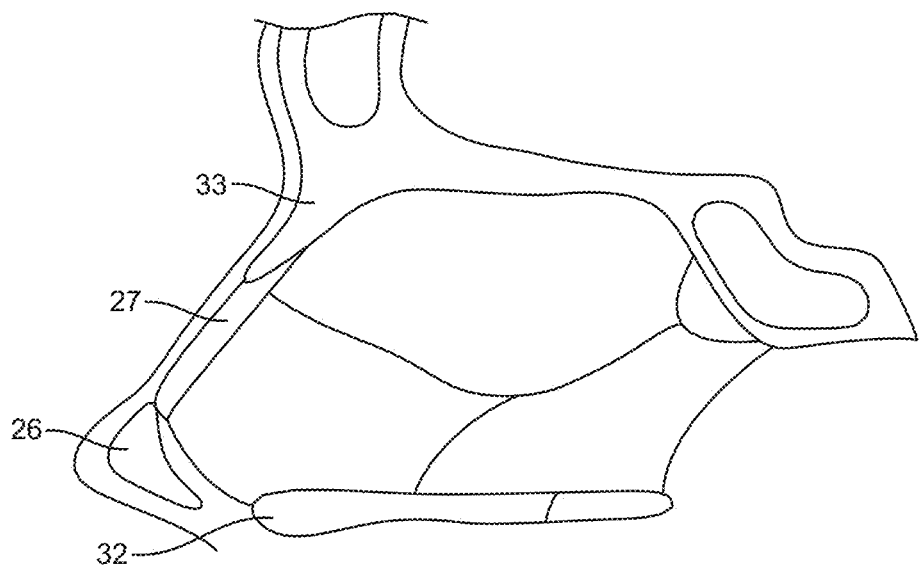
FIG. 7B depicts a side view of a subject's nasal cavity.

FIG. 7A depicts a side view of an exemplary embodiment of a representation subject's sinus. In some cases, the subject's sinus comprises the inferior turbinate 16, middle turbinate 15, superior turbinate 14, cribriform plate 31, middle meatus 30, or a combination thereof FIG. 7B depicts a side view of an exemplary embodiment of a representation subject's nasal cavity. In some embodiments, the nasal cavity 11 comprises the nasal bone 33, septal-lateral cartilage junction 27, lower lateral cartilage 26, anterior nasal spine 32, or a combination thereof.

Methods of Delivering a Fluid

Figure 8:
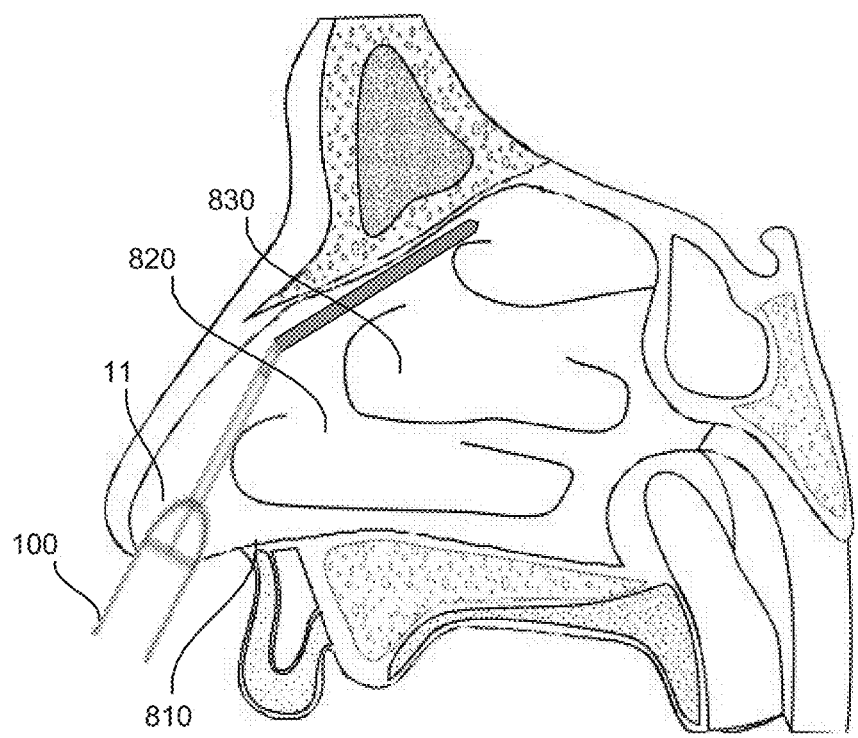
FIG. 8 depicts targeted delivery of a fluid to targeted subregion of a subject's nasal cavity.

In one aspect, per FIG. 8, is a method of delivering a fluid to a targeted sub-region of a subject's nasal cavity. In some embodiments, the fluid has a viscosity of less than about 3000 centipoise (cP). In some embodiments, the method comprises: a) ejecting a discrete volume of the fluid as a continuous stream from a dispensing element of a device; b) moving the continuous stream through an airspace in the nasal cavity towards the targeted sub-region; c) contacting an anatomical feature of the subject's nasal cavity with the continuous stream and forcing the fluid to move around the anatomical feature and towards the targeted sub-region; and d) contacting the targeted sub-region of the subject's nasal cavity with the fluid, thereby delivering the fluid to the targeted sub-region of the subject's nasal cavity. In some embodiments, the dispensing element comprises a cannula contained therein through which the fluid flows. In some embodiments, the cannula is entirely contained within the dispensing element. In some embodiments, the end of the cannula is coextensive with the end of the dispensing element.

In some embodiments, the method of delivering a fluid to a targeted sub-region of a subject's nasal cavity comprises ejecting a discrete volume of the fluid as a continuous stream from a dispensing element of a device, wherein the continuous stream travels through an airspace in the nasal cavity, contacts an anatomical feature of the subject's nasal cavity distal to the target sub-region, and travels along the anatomical feature to the targeted sub-region of the subject's nasal cavity. In some embodiments, the feature of the nasal cavity is a septum. In some embodiments, the method of delivering a fluid to a targeted sub-region of a subject's nasal cavity comprises ejecting a discrete volume of the fluid as a continuous stream from a dispensing element of a device towards the olfactory cleft, and does not substantially contact the middle turbinate or the superior turbinate with the fluid In some embodiments, a diameter of the continuous stream is about 1 mm to about 10 mm upon the ejecting from the dispensing element. In some embodiments, a diameter of the continuous stream is about 0.3 mm to about 6 mm the ejecting from the dispensing element. In some embodiments, the fluid comprises a medicament. In some embodiments, the medicament comprises a biologic, a protein, a nucleic acid, a vaccine, or a large molecule drug. In some embodiments, the medicament comprises a small molecule drug. In some embodiments, the ejecting of the discrete volume of the fluid occurs at a velocity of up to 50 m/s. In some embodiments, the ejecting of the discrete volume of the fluid occurs at a velocity of at least 1 m/s. In some embodiments, the ejecting of the discrete volume of the fluid occurs at a velocity of at least 10 m/s. In some embodiments, the ejecting of the discrete volume of the fluid occurs at a velocity of 10-50 m/s.

FIG. 1 shows an image of an exemplary dispensing element. In some embodiments, the dispensing element comprises an unobstructed opening at the tip of the dispensing element. In some embodiments, the dispensing element does not comprise an atomizer. In some embodiments, the dispensing element comprises an open channel. In some embodiments, the dispensing element delivers a continuous liquid stream. In some embodiments, the dispensing element delivers a continuous liquid stream with substantially no gaseous component. In some embodiments, the dispensing element delivers a continuous liquid stream with a gas component by volume not exceeding about 35%. In some embodiments, the dispensing element delivers a continuous liquid stream with a gas component by volume not exceeding about 35% at 5 mm from the dispensing tip. In some embodiments, the dispensing element delivers a continuous liquid stream with minimal gaseous component to enable the highly targeted delivery of fluid within the nasal cavity.

In some embodiments, the fluid is a low viscosity fluid. In some embodiments, the viscosity of the fluid is about 1 cP to about 3,000 cP. In some embodiments, the viscosity of the fluid is about 1 cP to about 10 cP, about 1 cP to about 25 cP, about 1 cP to about 50 cP, about 1 cP to about 75 cP, about 1 cP to about 100 cP, about 1 cP to about 250 cP, about 1 cP to about 500 cP, about 1 cP to about 1,000 cP, about 1 cP to about 1,500 cP, about 1 cP to about 2,000 cP, about 1 cP to about 3,000 cP, about 10 cP to about 25 cP, about 10 cP to about 50 cP, about 10 cP to about 75 cP, about 10 cP to about 100 cP, about 10 cP to about 250 cP, about 10 cP to about 500 cP, about 10 cP to about 1,000 cP, about 10 cP to about 1,500 cP, about 10 cP to about 2,000 cP, about 10 cP to about 3,000 cP, about 25 cP to about 50 cP, about 25 cP to about 75 cP, about 25 cP to about 100 cP, about 25 cP to about 250 cP, about 25 cP to about 500 cP, about 25 cP to about 1,000 cP, about 25 cP to about 1,500 cP, about 25 cP to about 2,000 cP, about 25 cP to about 3,000 cP, about 50 cP to about 75 cP, about 50 cP to about 100 cP, about 50 cP to about 250 cP, about 50 cP to about 500 cP, about 50 cP to about 1,000 cP, about 50 cP to about 1,500 cP, about 50 cP to about 2,000 cP, about 50 cP to about 3,000 cP, about 75 cP to about 100 cP, about 75 cP to about 250 cP, about 75 cP to about 500 cP, about 75 cP to about 1,000 cP, about 75 cP to about 1,500 cP, about 75 cP to about 2,000 cP, about 75 cP to about 3,000 cP, about 100 cP to about 250 cP, about 100 cP to about 500 cP, about 100 cP to about 1,000 cP, about 100 cP to about 1,500 cP, about 100 cP to about 2,000 cP, about 100 cP to about 3,000 cP, about 250 cP to about 500 cP, about 250 cP to about 1,000 cP, about 250 cP to about 1,500 cP, about 250 cP to about 2,000 cP, about 250 cP to about 3,000 cP, about 500 cP to about 1,000 cP, about 500 cP to about 1,500 cP, about 500 cP to about 2,000 cP, about 500 cP to about 3,000 cP, about 1,000 cP to about 1,500 cP, about 1,000 cP to about 2,000 cP, about 1,000 cP to about 3,000 cP, about 1,500 cP to about 2,000 cP, about 1,500 cP to about 3,000 cP, or about 2,000 cP to about 3,000 cP, including increments therein. In some embodiments, the viscosity of the fluid is about 1 cP, about 10 cP, about 25 cP, about 50 cP, about 75 cP, about 100 cP, about 250 cP, about 500 cP, about 1,000 cP, about 1,500 cP, about 2,000 cP, or about 3,000 cP. In some embodiments, the viscosity of the fluid is at least about 1 cP, about 10 cP, about 25 cP, about 50 cP, about 75 cP, about 100 cP, about 250 cP, about 500 cP, about 1,000 cP, about 1,500 cP, or about 2,000 cP. In some embodiments, the viscosity of the fluid is at most about 10 cP, about 25 cP, about 50 cP, about 75 cP, about 100 cP, about 250 cP, about 500 cP, about 1,000 cP, about 1,500 cP, about 2,000 cP, or about 3,000 cP. Targeted delivery of a low viscosity fluid within the nasal cavity presents a number of challenges due to the tendency of low viscosity fluids to deflect about features of the nasal cavity and flow into off-target regions. Including, for example, when the low viscosity fluid contacts a feature of the nasal anatomy, or flows from a targeted region to an off-target region. The methods disclosed herein can provide for the targeted delivery of low viscosity fluids to targeted subregions of the nasal cavity. The methods disclosed herein can provide for the targeted delivery of low viscosity fluids to targeted subregions of the nasal cavity by ejecting discrete volumes of the fluid as a continuous liquid stream. The continuous liquid stream may be ejected along a trajectory such that the fluid contacts the targeted subregion, and substantially avoids off-target regions. The continuous liquid stream may be ejected in a discrete volume such that the fluid does not flow from a targeted subregion to an off-target subregion of the nasal cavity following deposition of the fluid on the targeted subregion.

In some embodiments, at a distance of about 5 mm from the dispensing tip, a flux through a planar surface orthogonal to a flow path of the continuous stream possesses a gas component by volume of less than about 35%, 30%, 25%, 20%, 15%, 10%, 5%, 1%, or less, including increments therein. In some embodiments, at a distance of about 5 mm from the dispensing tip, a flux through a planar surface orthogonal to a flow path of the continuous stream possesses a gas component by volume of less than about 1% to about 35%. In some embodiments, at a distance of about 5 mm from the dispensing tip, a flux through a planar surface orthogonal to a flow path of the continuous stream possesses a gas component by volume of less than about 1% to about 3%, about 1% to about 7%, about 1% to about 9%, about 1% to about 10%, about 1% to about 12%, about 1% to about 15%, about 1% to about 18%, about 1% to about 22%, about 1% to about 25%, about 1% to about 30%, about 1% to about 35%, about 3% to about 7%, about 3% to about 9%, about 3% to about 10%, about 3% to about 12%, about 3% to about 15%, about 3% to about 18%, about 3% to about 22%, about 3% to about 25%, about 3% to about 30%, about 3% to about 35%, about 7% to about 9%, about 7% to about 10%, about 7% to about 12%, about 7% to about 15%, about 7% to about 18%, about 7% to about 22%, about 7% to about 25%, about 7% to about 30%, about 7% to about 35%, about 9% to about 10%, about 9% to about 12%, about 9% to about 15%, about 9% to about 18%, about 9% to about 22%, about 9% to about 25%, about 9% to about 30%, about 9% to about 35%, about 10% to about 12%, about 10% to about 15%, about 10% to about 18%, about 10% to about 22%, about 10% to about 25%, about 10% to about 30%, about 10% to about 35%, about 12% to about 15%, about 12% to about 18%, about 12% to about 22%, about 12% to about 25%, about 12% to about 30%, about 12% to about 35%, about 15% to about 18%, about 15% to about 22%, about 15% to about 25%, about 15% to about 30%, about 15% to about 35%, about 18% to about 22%, about 18% to about 25%, about 18% to about 30%, about 18% to about 35%, about 22% to about 25%, about 22% to about 30%, about 22% to about 35%, about 25% to about 30%, about 25% to about 35%, or about 30% to about 35%, including increments therein. In some embodiments, at a distance of about 5 mm from the dispensing tip, a flux through a planar surface orthogonal to a flow path of the continuous stream possesses a gas component by volume of less than about 1%, about 3%, about 7%, about 9%, about 10%, about 12%, about 15%, about 18%, about 22%, about 25%, about 30%, or about 35%. In some embodiments, at a distance of about 5 mm from the dispensing tip, a flux through a planar surface orthogonal to a flow path of the continuous stream possesses a gas component by volume of less than at least about 1%, about 3%, about 7%, about 9%, about 10%, about 12%, about 15%, about 18%, about 22%, about 25%, or about 30%. In some embodiments, at a distance of about 5 mm from the dispensing tip, a flux through a planar surface orthogonal to a flow path of the continuous stream possesses a gas component by volume of less than at most about 3%, about 7%, about 9%, about 10%, about 12%, about 15%, about 18%, about 22%, about 25%, about 30%, or about 35%.

In some embodiments, the continuous stream of the fluid is ejected from the dispensing element at a velocity of about 2 m/s to about 20 m/s. In some embodiments, the continuous stream of the fluid is ejected from the dispensing element at a velocity of about 2 m/s to about 3 m/s, about 2 m/s to about 4 m/s, about 2 m/s to about 5 m/s, about 2 m/s to about 6 m/s, about 2 m/s to about 8 m/s, about 2 m/s to about 10 m/s, about 2 m/s to about 12 m/s, about 2 m/s to about 14 m/s, about 2 m/s to about 16 m/s, about 2 m/s to about 18 m/s, about 2 m/s to about 20 m/s, about 3 m/s to about 4 m/s, about 3 m/s to about 5 m/s, about 3 m/s to about 6 m/s, about 3 m/s to about 8 m/s, about 3 m/s to about 10 m/s, about 3 m/s to about 12 m/s, about 3 m/s to about 14 m/s, about 3 m/s to about 16 m/s, about 3 m/s to about 18 m/s, about 3 m/s to about 20 m/s, about 4 m/s to about 5 m/s, about 4 m/s to about 6 m/s, about 4 m/s to about 8 m/s, about 4 m/s to about 10 m/s, about 4 m/s to about 12 m/s, about 4 m/s to about 14 m/s, about 4 m/s to about 16 m/s, about 4 m/s to about 18 m/s, about 4 m/s to about 20 m/s, about 5 m/s to about 6 m/s, about 5 m/s to about 8 m/s, about 5 m/s to about 10 m/s, about 5 m/s to about 12 m/s, about 5 m/s to about 14 m/s, about 5 m/s to about 16 m/s, about 5 m/s to about 18 m/s, about 5 m/s to about 20 m/s, about 6 m/s to about 8 m/s, about 6 m/s to about 10 m/s, about 6 m/s to about 12 m/s, about 6 m/s to about 14 m/s, about 6 m/s to about 16 m/s, about 6 m/s to about 18 m/s, about 6 m/s to about 20 m/s, about 8 m/s to about 10 m/s, about 8 m/s to about 12 m/s, about 8 m/s to about 14 m/s, about 8 m/s to about 16 m/s, about 8 m/s to about 18 m/s, about 8 m/s to about 20 m/s, about 10 m/s to about 12 m/s, about 10 m/s to about 14 m/s, about 10 m/s to about 16 m/s, about 10 m/s to about 18 m/s, about 10 m/s to about 20 m/s, about 12 m/s to about 14 m/s, about 12 m/s to about 16 m/s, about 12 m/s to about 18 m/s, about 12 m/s to about 20 m/s, about 14 m/s to about 16 m/s, about 14 m/s to about 18 m/s, about 14 m/s to about 20 m/s, about 16 m/s to about 18 m/s, about 16 m/s to about 20 m/s, or about 18 m/s to about 20 m/s, including increments therein. In some embodiments, the continuous stream of the fluid is ejected from the dispensing element at a velocity of about 2 m/s, about 3 m/s, about 4 m/s, about 5 m/s, about 6 m/s, about 8 m/s, about 10 m/s, about 12 m/s, about 14 m/s, about 16 m/s, about 18 m/s, or about 20 m/s. In some embodiments, the continuous stream of the fluid is ejected from the dispensing element at a velocity of at least about 2 m/s, about 3 m/s, about 4 m/s, about 5 m/s, about 6 m/s, about 8 m/s, about 10 m/s, about 12 m/s, about 14 m/s, about 16 m/s, or about 18 m/s. In some embodiments, the continuous stream of the fluid is ejected from the dispensing element at a velocity of at most about 3 m/s, about 4 m/s, about 5 m/s, about 6 m/s, about 8 m/s, about 10 m/s, about 12 m/s, about 14 m/s, about 16 m/s, about 18 m/s, or about 20 m/s. In some embodiments, the continuous stream of the fluid is ejected from the dispensing element at a velocity of up to 50 m/s.

In some embodiments, the discrete volume of the fluid is about 25 μL to about 225 μL. In some embodiments, the discrete volume of the fluid is about 25 μL to about 50 μL, about 25 μL to about 75 μL, about 25 μL to about 100 μL, about 25 μL to about 125 μL, about 25 μL to about 150 μL, about 25 μL to about 175 μL, about 25 μL to about 200 μL, about 25 μL to about 225 μL, about 50 μL to about 75 μL, about 50 μL to about 100 μL, about 50 μL to about 125 μL, about 50 μL to about 150 μL, about 50 μL to about 175 μL, about 50 μL to about 200 μL, about 50 μL to about 225 μL, about 75 μL to about 100 μL, about 75 μL to about 125 μL, about 75 µL to about 150 µL, about 75 µL to about 175 µL, about 75 µL to about 200 µL, about 75 µL to about 225 µL, about 100 µL to about 125 µL, about 100 µL to about 150 µL, about 100 µL to about 175 µL, about 100 µL to about 200 µL, about 100 µL to about 225 µL, about 125 µL to about 150 µL, about 125 µL to about 175 µL, about 125 µL to about 200 µL, about 125 µL to about 225 µL, about 150 µL to about 175 µL, about 150 µL to about 200 µL, about 150 µL to about 225 µL, about 175 µL to about 200 µL, about 175 µL to about 225 µL, or about 200 µL to about 225 µL, including increments therein. In some embodiments, the discrete volume of the fluid is about 25 µL, about 50 µL, about 75 µL, about 100 µL, about 125 µL, about 150 µL, about 175 µL, about 200 µL, or about 225 µL. In some embodiments, the discrete volume of the fluid is at least about 25 µL, about 50 µL, about 75 µL, about 100 µL, about 125 µL, about 150 µL, about 175 µL, or about 200 µL. In some embodiments, the discrete volume of the fluid is at most about 50 µL, about 75 µL, about 100 µL, about 125 µL, about 150 µL, about 175 µL, about 200 µL, or about 225 µL.

In some embodiments, the ejecting the continuous stream of the fluid from the dispensing element results in a change in a velocity of the fluid of less than about 25%, 20%, 15%, 10%, 5%, 1% or less, including increments therein within about 5 mm from its point of ejection.

In some embodiments, a diameter of the continuous stream is about 1 mm to about 10 mm upon the ejecting from the dispensing element. In some embodiments, a diameter of the continuous stream is about 1 mm to about 6 mm upon the ejecting from the dispensing element. In some embodiments, a diameter of the continuous stream is about 0.3 mm to about 6 mm the ejecting from the dispensing element. In some embodiments, the fluid comprises a medicament. In some embodiments, the medicament comprises a biologic, a protein, a nucleic acid, a vaccine, or a large molecule drug. In some embodiments, the medicament comprises a small molecule drug. In some embodiments, the ejecting of the discrete volume of the fluid occurs at a velocity of up to 50 m/s.

In some embodiments, the method does not result in substantial deposition of the fluid in a region of the subject's nasal cavity, which is not the targeted sub-region, immediately following the contacting of step (d). In some embodiments, the method results in less than about 10% of the fluid being deposited in a region of the subject's nasal cavity, which is not the targeted sub-region, immediately following the contacting of step (d). In some embodiments, the method results in less than about 0.1%, 1%, or 5% of the fluid being deposited in a region of the subject's nasal cavity, which is not the targeted sub-region, immediately following the contacting of step (d). In some embodiments, forcing the fluid to move around the anatomical feature comprises changing a direction of movement of the fluid relative to a direction of movement of the fluid in (b).

In some embodiments, the ejecting the discrete volume of the fluid as the continuous stream ejects the continuous stream in a vector which has a vorticity vector having a magnitude of less than about 0.2× of a magnitude of a velocity vector of the continuous stream at the time of the ejecting from the dispensing element. In some embodiments, moving the continuous stream through the airspace in the nasal cavity occurs along a vector having a vorticity vector having a magnitude of less than about 0.2× of a magnitude of a velocity vector of the continuous stream at the time of the ejecting from the dispensing element. In some embodiments, the continuous stream is ejected in a non-rotating vector. In some embodiments, vorticity ($\vec{\omega}$) is defined by a cross product of a directional derivative vector ($\nabla$) of the continuous stream and the velocity vector ($\vec{u}$) of the continuous stream (e.g., $\vec{\omega} = \nabla \times \vec{u}$). In some embodiments, the z-component of ω satisfies:

$$\|\omega_2\|_2 = \left\|\frac{\partial v(x, y, z)}{\partial x} - \frac{\partial u(x, y, z)}{\partial y}\right\|_2 < 0.2 \cdot \|\vec{u}\|_2$$

where $\|\cdot\|_2$ is the Euclidean 2-norm. In some embodiments, the magnitude of the vorticity vector is reported as an absolute value. In some embodiments, limiting the vorticity of the continuous liquid stream promotes on target deposition of the fluid to the targeted subregion, and minimizes off-target deposition of the fluid. In some embodiments, ejecting the continuous liquid stream in a non-rotating vector increases the on target deposition of the fluid to the targeted subregion, and minimizes off-target deposition of the fluid. In some embodiments, the ejecting the discrete volume of the fluid as the continuous stream ejects the continuous stream in a velocity vector of the continuous stream which has a vorticity of less than about 0.2× the magnitude of the velocity vector at the time of the ejecting from the dispensing element. In some embodiments, the moving the continuous stream through the airspace in the nasal cavity occurs along a velocity vector of the continuous stream which has a vorticity of less than about 0.2× the magnitude of the velocity vector at the time of the ejecting from the dispensing element.

In some embodiments, the continuous stream moves through the airspace in the nasal cavity before contacting the targeted subregion for a distance of at least about 0.1 cm, 0.2 cm, 0.3 cm, 0.4 cm, 0.5 cm, or more, including increments therein. In some embodiments, at least about 65%, 70%, 75%, 80%, 85%, 90%, including increments therein, or more, of the continuous stream is directed within the target region. In some embodiments, less than about 15%, 10%, 8%, 6%, 4%, or less, of the continuous stream is directed outside the target region, including increments therein.

Bolus Deposition Patterns

A bolus refers to a contiguous mass or dose of a liquid formulation. A bolus deposition refers to a contiguous mass or dose of a liquid formulation which is delivered in a single, concentrated amount, within the nasal cavity. A bolus deposition pattern can be described as a deposition pattern in which most or all of the fluid is retained as a cohesive liquid mass upon deposition of the fluid at rest. In some embodiments, depositing the fluid as a bolus deposition pattern promotes on target deposition of the fluid to the targeted subregion, and minimizes off-target deposition of the fluid. In some embodiments, depositing the fluid as a bolus deposition pattern promotes on target deposition of the fluid to the targeted subregion, wherein the targeted subregion is the olfactory cleft.

A bolus deposition pattern may be ideal for delivery to the olfactory cleft and individual turbinates/conches. A bolus deposition pattern may be ideal for cases where highly specific deposition is required with minimized exposure to other regions. A bolus deposition pattern may be ideal for targeting particular subregions of the nasal cavity, as it deposits most of the fluid to single subregion of the nasal cavity. Similarly, the bolus deposition pattern may be ideal for minimizing off target delivery, as it prevents deposition of the fluid to regions of the nasal cavity other than the single subregion. A bolus deposition pattern may be ideal for targeting delivery of a fluid to an olfactory region of the nasal cavity, as illustrated in FIGS. 16D and 17G. A bolus deposition pattern may be ideal for cases where a slower release of medication is required to be absorbed/diffuse through the mucosal membrane or anatomical structure. A bolus deposition pattern may be ideal for cases where a sustained release of medication is desired, such as delivery of a therapeutic agent across the olfactory cleft. A bolus deposition pattern may be ideal for cases where a sustained release of medication is desired, such as delivery of a therapeutic agent across the olfactory cleft and into the cerebral spinal fluid or central nervous system. A bolus deposition pattern may be ideal for cases where absorption is required over a longer period of time due to a short half-life of a drug. The mass of the bolus delivered directly to the olfactory cleft may provide for sustained direct-to-brain diffusion while minimizing and an increased therapeutic response due to the action of a drug in the brain, and reduced systemic exposure due to minimizing the lower nasal cavity exposure thereby lowering plasma concentrations of the drug resulting from traditional mucosal delivery routes.

In some embodiments, the fluid contacts the targeted sub-region of the subject's nasal cavity with the fluid in a bolus deposition pattern. In some embodiments, the bolus deposition pattern comprises deposition of the continuous stream onto the targeted sub-region in a cohesive liquid mass. In some embodiments, the cohesive liquid mass comprises at least about 50%, 55%, 60%, 65%, 70%, 75%, 80%, or more, including increments therein, of the fluid ejected from the dispensing element. In some embodiments, the bolus deposition pattern comprises at most about 5%, 10%, 15%, 20%, or less, including increments therein, of droplets. In some embodiments, the bolus deposition pattern comprises deposition of the continuous stream onto the targeted sub-region without substantial formation of droplets, immediately following the contacting of step (d).

Figure 12A:
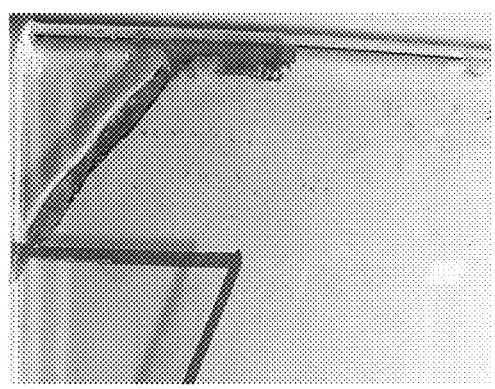
FIG. 12A illustrates an initial state of a low viscosity fluid upon striking a curved glass sheet and prior to forming a bolus deposition pattern, per one or more embodiments herein.
Figure 12B:
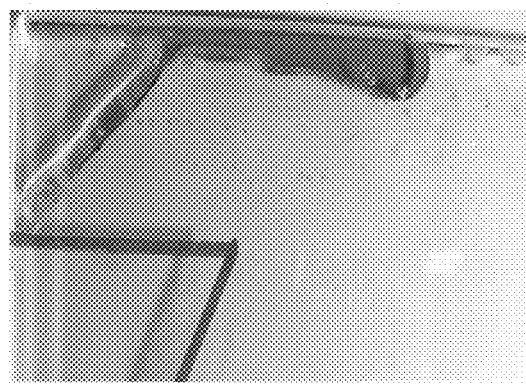
FIG. 12B illustrates an intermediate state of a low viscosity fluid after striking a curved glass sheet following impact and prior to forming a bolus deposition pattern, per one or more embodiments herein.
Figure 12C:
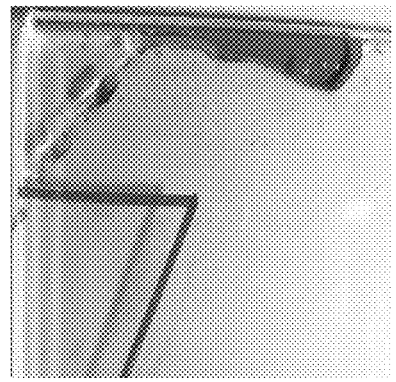
FIG. 12C illustrates a final state of a low viscosity fluid after striking a curved glass sheet and coming to rest in a bolus deposition pattern, per one or more embodiments herein.

In some embodiments, the continuous stream of the fluid at the point of ejection from the dispensing element has a Reynolds number of less than about 2,000, 1,750, 1,500, 1,250, 1,000, 750, 500, 250 or less, including increments therein. FIG. 12A illustrates an initial state of a low viscosity fluid upon striking a curved glass sheet and did not form a bolus deposition pattern, at a velocity of 1.54 m/s. FIG. 12B illustrates an intermediate state of a low viscosity fluid after striking a curved glass sheet following impact and did not form a bolus deposition pattern at a velocity of 1.54 m/s. FIG. 12C illustrates a final state of a low viscosity fluid after striking a curved glass sheet and did not form a bolus deposition pattern, at a velocity of 1.54 m/s. Similar results are shown in FIGS. 15A-15C, in which a fully formed liquid bolus in the target location did not form at the low ejection velocity of 5.78 m/s.

FIG. 15A illustrates an initial state of a high viscosity fluid upon striking a curved glass sheet and prior to forming a bolus deposition pattern at a velocity of 5.78 m/s, failing to form bolus deposition pattern. FIG. 15B illustrates a high viscosity in an intermediate state of a fluid after striking a curved glass sheet following impact 5.78 m/s and prior to forming a bolus deposition pattern. FIG. 15C illustrates a final state of a high viscosity fluid after striking a curved glass sheet at 5.78 m/s failing to form bolus deposition pattern. FIGS. 15A-15C illustrate that the ejection velocity was too low and a liquid bolus did not form in the target location, as the fluid coalesced in front of the tip of the liquid sheet.

FIGS. 15A-15I show exemplary image of fluid hitting an increased 50 cP viscosity fluid hitting curved glass sheet, and forming a bolus deposition pattern. FIG. 15D shows an exemplary image of fluid hitting a curved glass sheet at a velocity of 11.5 m/s prior to forming a bolus deposition pattern. FIG. 15E shows an exemplary image of intermediate ejection at a velocity of 11.5 m/s prior to forming in a bolus deposition pattern. FIG. 15F shows an exemplary image of final ejection at a velocity of 11.5 m/s coming to rest and resulting in a bolus deposition pattern. FIG. 15G shows an exemplary image of fluid hitting a curved glass sheet at a velocity of 13.27 m/s prior to resulting in a bolus deposition pattern. FIG. 15H shows an exemplary image of intermediate ejection at a velocity of 13.27 m/s prior to resulting in a bolus deposition pattern. FIG. 15I shows an exemplary image of final ejection at a velocity of 13.27 m/s coming to rest and resulting in a bolus deposition pattern.

As is shown in FIGS. 15D-15I, a bolus deposition may be ideal for deposition to the olfactory cleft and may allow for targeted deposition of a fluid to the olfactory cleft while minimizing off-target delivery. As is shown in FIGS. 15D-15I, may be achieved at increased ejection velocities, in some cases exceeding 11.5 m/s with a fluid having a viscosity of about 50 cP. A bolus deposition may be ideal for deposition to the olfactory cleft and may allow for targeted deposition of a fluid to the olfactory cleft while minimizing off-target delivery.

Transitory Deposition Patterns

A transitory deposition pattern can be described as a deposition pattern in which the fluid is in between a bolus deposition pattern, and a surface deposition pattern. It may comprise characteristics of both the liquid bolus deposition pattern, and a surface deposition pattern. A transitory deposition pattern may not achieve the highly targeted delivery of a fluid achieved by a bolus deposition pattern, and may also not achieve the widely distributed pattern of surface deposition described below.

Figure 13A:
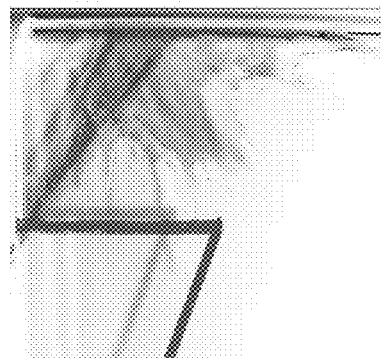
FIG. 13A illustrates an initial state of a low viscosity fluid upon striking a curved glass sheet and prior to forming a transitory deposition pattern, per one or more embodiments herein.
Figure 13D:
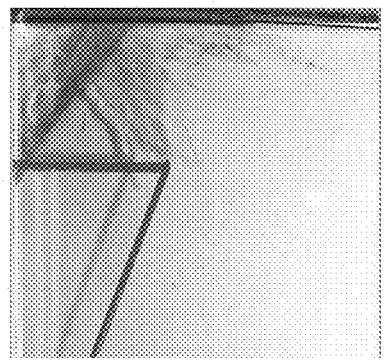
FIG. 13D illustrates an initial state of a low viscosity fluid upon striking a curved glass sheet and prior to forming a transitory deposition pattern, per one or more embodiments herein.
Figure 13B:
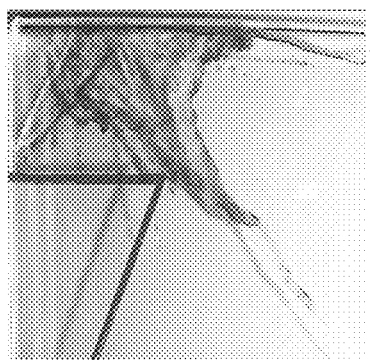
FIG. 13B illustrates an intermediate state of a low viscosity fluid after striking a curved glass sheet following impact and prior to forming a transitory deposition pattern, per one or more embodiments herein.
Figure 13E:
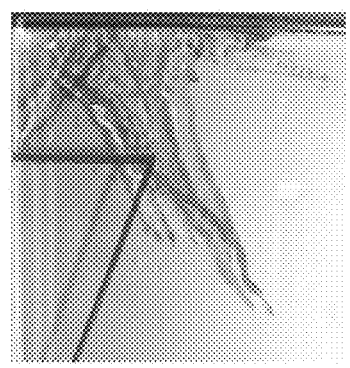
FIG. 13E illustrates an intermediate state of a low viscosity fluid after striking a curved glass sheet following impact and prior to forming a transitory deposition pattern, per one or more embodiments herein.
Figure 13C:
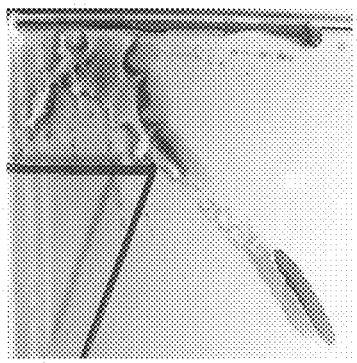
FIG. 13C illustrates a final state of a low viscosity fluid after striking a curved glass sheet and coming to rest in and forming a transitory deposition pattern, per one or more embodiments herein.
Figure 13F:
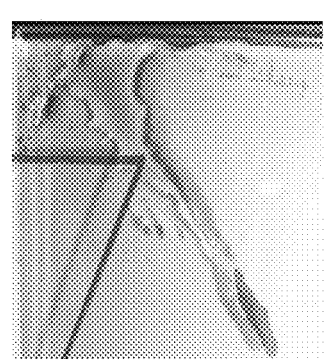
FIG. 13F illustrates a final state of a low viscosity fluid after striking a curved glass sheet and coming to rest and forming a transitory deposition pattern, per one or more embodiments herein.

In some embodiments, the fluid is deposited onto the targeted sub-region transitory deposition patterns. FIG. 13A shows an exemplary image of fluid hitting a curved glass sheet at a velocity of 3 m/s prior to forming a transitory deposition pattern. FIG. 13B shows an exemplary image of intermediate ejection at a velocity of 3 m/s prior to forming a transitory deposition pattern. FIG. 13C shows an exemplary image of a final state at an ejection velocity of 3 m/s forming a transitory deposition pattern. FIG. 13D shows an exemplary image of fluid hitting a curved glass sheet during ejection at a velocity of 5.6 m/s prior to forming a transitory deposition pattern. FIG. 13E shows an exemplary image of intermediate ejection at a velocity of 5.6 m/s prior to forming a transitory deposition pattern. FIG. 13F shows an exemplary image of a final state at an ejection velocity of 5.6 m/s forming a transitory deposition pattern. In some embodiments, the continuous liquid stream is not deposited in a transitory deposition pattern within the nasal cavity.

Surface Deposition Patterns

A surface deposition pattern can be described as a deposition pattern in which the fluid is distributed across a wide area in a substantially continuous liquid sheet. Surface deposition of a liquid refers to the process by which a liquid formulation is deposited or adheres to the mucosal membranes, forming a layer or film, within the nasal cavity. A surface deposition pattern may be ideal for targeting larger subregions of the nasal cavity, as it reliably deposits the fluid across a wide area. Similarly, the surface deposition pattern may be ideal for minimizing off target delivery to regions of the nasal cavity which are not easily reachable (e.g., are obstructed by anatomical features). A surface deposition pattern may be ideal for targeting the nasal mucosa, the olfactory cleft, the middle turbinate, the superior turbinate, or the lower turbinate. A surface deposition pattern may be ideal where specific, regional, or large surface area deposition is required, with minimized exposure to other regions. A surface deposition pattern may be ideal for cases where a fast release and/or high concentration of medication is required to be absorbed/diffuse through the mucosal membrane or anatomical structure. A surface deposition pattern may be ideal in cases where a higher volume or surface contact absorption is required over a short time (e.g., vaccine delivery to the turbinates). The surface area deposition allows for rapid exposure and interactions with a large number of immune cells due to the high volume-surface contact ratio, while minimizing off-target exposure such as olfactory involvement olfactory and possible undesirable immune response.

Figure 11B:
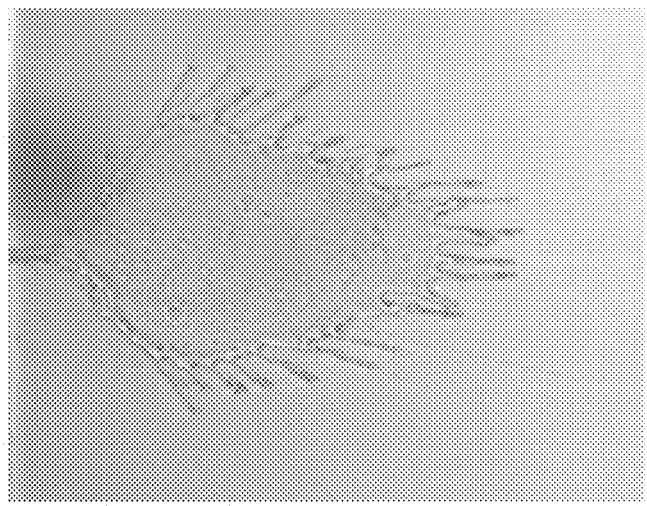
FIG. 11B shows an exemplary image of an impact wave fluid formation, per one or more embodiments herein.
Figure 11A:
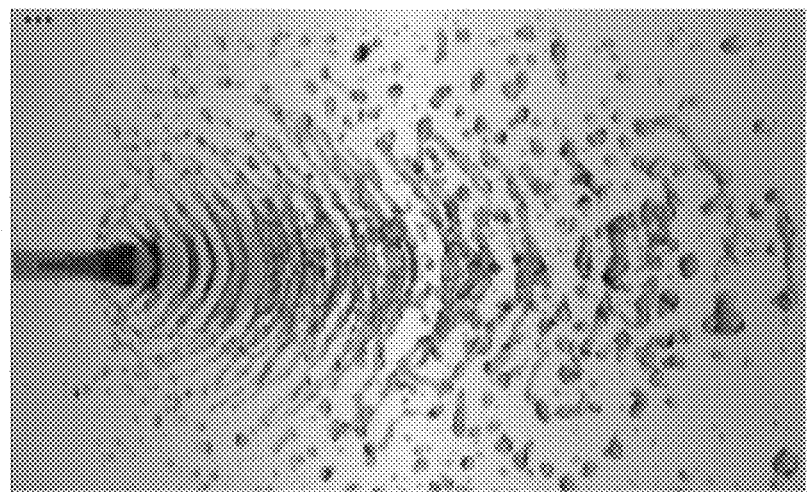
FIG. 11A shows an exemplary image of an impact wave fluid formation, per one or more embodiments herein.

In some embodiments, the surface deposition pattern comprises deposition of the continuous stream onto the targeted sub-region in a liquid sheet. In some embodiments, the liquid sheet comprises less than about 10% of the fluid ejected forming droplets. In some embodiments, the liquid sheet comprises substantially no droplets. FIG. 11A shows an exemplary image of droplet formation of impact waves upon ejection with a velocity of 11.2 m/s, which may result in a surface deposition pattern. FIG. 11B shows an exemplary image of droplet formation of an impact wave upon ejection with a velocity of 11.5 m/s, which may result in a surface deposition pattern.

Figure 14A:
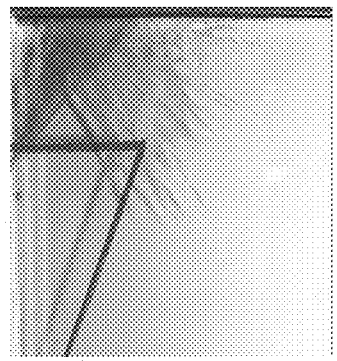
FIG. 14A illustrates an initial state of a low viscosity fluid upon striking a curved glass sheet and prior to forming a surface deposition pattern, per one or more embodiments herein.
Figure 14D:
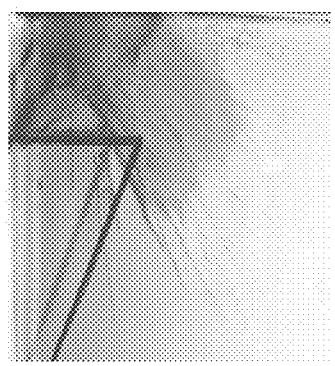
FIG. 14D illustrates an initial state of a low viscosity fluid upon striking a curved glass sheet and prior to forming a droplet deposition pattern, per one or more embodiments herein.
Figure 14B:
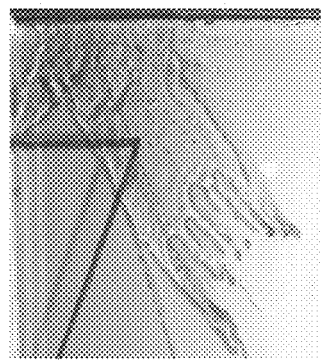
FIG. 14B illustrates a an intermediate state of a low viscosity fluid after striking a curved glass sheet following impact and prior to forming a surface deposition pattern, per one or more embodiments herein.
Figure 14E:
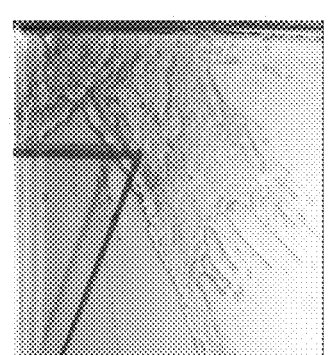
FIG. 14E illustrates a an intermediate state of a low viscosity fluid after striking a curved glass sheet following impact and prior to forming a droplet deposition pattern, per one or more embodiments herein.
Figure 14C:
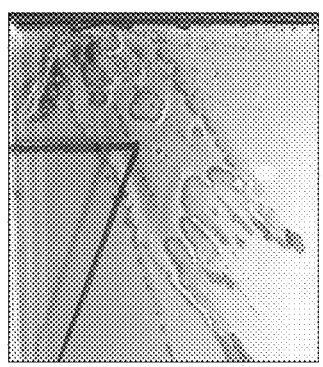
FIG. 14C illustrates a final state of a low viscosity fluid after striking a curved glass sheet and coming to rest and forming a surface deposition pattern, per one or more embodiments herein.

In some embodiments, the fluid is deposited onto the targeted sub-region in a surface deposition pattern. FIG. 14A illustrates an initial state of a low viscosity fluid upon striking a curved glass sheet and prior to forming a surface deposition pattern, when ejected at a velocity of 7.6 m/s. FIG. 14B illustrates an intermediate state of a low viscosity fluid after striking a curved glass sheet following impact and prior to forming a surface deposition pattern, when ejected at a velocity of 7.6 m/s. FIG. 14C illustrates a final state of a low viscosity fluid after striking a curved glass sheet and coming to rest and forming a surface deposition pattern, when ejected at a velocity of 7.6 m/s.

Droplet Deposition Patterns

Droplet deposition of a liquid refers to the process by which droplets of the liquid formulation are formed during delivery from instabilities/impact waves formed in the liquid sheet, and are deposited on the mucosal membranes, forming a pattern or layer of droplets, within the nasal cavity. The instability/impact waves formed in the liquid sheet on impingement with a target surface explodes the liquid dose to coat the target area in a layer of droplets with a high volume-surface contact ratio that maximizes the surface coverage of the drug. A droplet deposition pattern can be described as a deposition pattern in which the fluid is deposited within the nasal cavity in a plurality of large droplets across a subregion of the nasal cavity, with there being an uneven coating of the fluid across the subregion of the subregion nasal cavity. A droplet deposition pattern may not achieve the highly targeted delivery of a fluid achieved by a bolus deposition pattern and may also not achieve the widely distributed pattern of surface deposition. A droplet deposition pattern can be ideal for drug delivery to the olfactory cleft or individual turbinates/conches. A droplet deposition pattern can be ideal unspecific, multiple regions, large surface, and/or pathological anatomical structure deposition is required. A droplet deposition pattern can be ideal where a fast release, large surface coverage, and/or high concentration of medication is required to be absorbed/diffuse through the mucosal membrane or anatomical structure. For example, a droplet deposition pattern can be ideal where an unspecific, multiple region deposition of a topical steroid is required on a large surface, a pathological anatomical structure such as a nasal polyp, or on the epithelium of the polyp(s).

Figure 14F:
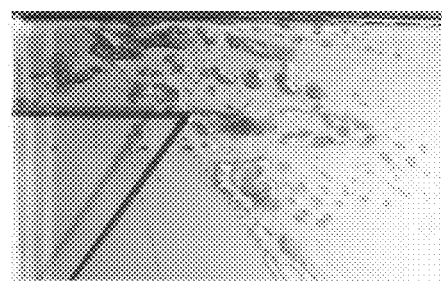
FIG. 14F illustrates a final state of a low viscosity fluid after striking a curved glass sheet and coming to rest and forming a droplet deposition pattern, per one or more embodiments herein.

In some embodiments, a droplet pattern comprises deposition of the continuous stream onto the targeted sub-region in a plurality of droplets. FIG. 14D shows an exemplary image of fluid hitting a curved glass sheet during droplet deposition at a velocity of 11.5 m/s. FIG. 14E shows an exemplary image of intermediate ejection during droplet deposition at a velocity of 11.5 m/s. FIG. 14F shows an exemplary image of final ejection during droplet deposition at a velocity of 11.5 m/s.

In some embodiments, ejecting the continuous stream of the fluid from the dispensing element results in the formation of fluid profile upon contacting a feature of the nasal anatomy. The fluid profile formed may comprise a liquid chain fluid profile, a semi-closed rim fluid profile, or a closed rim profile. In some embodiments, ejecting the continuous stream of the fluid from the dispensing element results in the formation of a liquid rim fluid profile upon the contacting of step (c). In some embodiments, the liquid rim fluid profile comprises a semi-closed rim fluid profile, an open rim fluid profile, or an unstable rim fluid profile. In some embodiments, ejecting the continuous stream of the fluid from the dispensing element results in the formation of an impact wave fluid profile upon the contacting of step (c). FIG. 9A shows an exemplary image of liquid chain formation with a velocity of 1.6 m/s. FIG. 9B shows an exemplary image of liquid chain formation with a velocity of 2.2 m/s. FIG. 9C shows an exemplary image of semi-closed rim formation with a velocity of 3.0 m/s. FIG. 9D shows an exemplary image of closed rim formation with a velocity of 3.3 m/s. FIG. 10A shows an exemplary image of an open rim surface coating with a velocity of 5.0 m/s. FIG. 10B shows an exemplary image of an open rim surface coating with a velocity of 5.3 m/s. FIG. 10C shows an exemplary image of unstable rim surface coating with a velocity of 7.6 m/s. FIG. 10D shows an exemplary image of an unstable rim surface coating with a velocity of 7.9 m/s.

Target Regions

In some embodiments, the targeted subregion is a middle turbinate of the subject. In some embodiments, contacting the middle turbinate comprises coating a surface of the middle turbinate. In some embodiments, contacting the middle turbinate partially fills a volume of the nasal cavity. In some embodiments, the targeted subregion is a middle turbinate of the subject, and wherein substantially none of the fluid is deposited outside the middle turbinate of the subject, immediately following the contacting of step (d). In some embodiments, contacting the middle turbinate comprises coating a surface of the middle turbinate. In some embodiments, contacting the middle turbinate partially fills a volume of the nasal cavity. In some embodiments, the targeted subregion is an olfactory cleft of the subject. In some embodiments, contacting the olfactory cleft comprises coating a surface of the olfactory cleft. In some embodiments, contacting the olfactory cleft comprises partially filling a volume of the nasal cavity. In some embodiments, the targeted subregion is an olfactory cleft of the subject, and wherein substantially none of the fluid is deposited outside of the olfactory cleft of the subject, immediately following the contacting of step (d). In some embodiments, the feature of the nasal cavity is a septum. In some embodiments, a capillary bridge is formed by the fluid, wherein the capillary bridge contacts opposing sides of an olfactory region of the subject's nasal cavity and supports a coating of the fluid about the olfactory cleft. In some embodiments, contacting the olfactory cleft comprises coating a surface of the olfactory cleft. In some embodiments, contacting the olfactory cleft comprises partially filling a volume of the nasal cavity. In some embodiments, a capillary bridge is formed by the fluid, wherein the capillary bridge contacts opposing sides of an olfactory region of the subject's nasal cavity and supports a coating of the fluid about the olfactory cleft.

EXAMPLES

Experimental Set Up and Introduction

Experiments were performed by ejecting a fluid jet from a dispensing element under differing ejection conditions as to induce different resulting surface deposition profiles. In these experiments, the jet column was seen to interact with the medial and/or lateral wall forming a diverging thin sheet with defined edges at a short distance (1-3 mm). At low ejection velocities with an exemplary low viscosity fluid, successful bolus depositions were found. It was also observed that on impact with a superior aspect of the structure modeling a nasal cavity, the fluid formed recirculating regions to form a coherent bolus. At medium velocities with an exemplary low viscosity fluid, it was observed that a surface coating was deposited and no coherent bolus was formed. At higher velocities with an exemplary low viscosity fluid, it was observed that the fluid exploded into a droplet deposition. At various ejection velocities with an exemplary increased viscosity fluid, successful bolus depositions were found under a variety of conditions. From research, the evolution of the flow was determined to be that of an impinging jet.

Figure 17A:
FIG. 17A illustrates an initial state of a high velocity fluid in a dispensing element in an exemplary nasal cavity model, per one or more embodiments herein.
Figure 17B:
FIG. 17B illustrates a sheet/rim formation state of a high velocity fluid contacting a medial wall of the olfactory cleft following ejection from the dispensing element, per one or more embodiments herein.
Figure 17C:
FIG. 17C illustrates a recirculation state of a high velocity fluid contacting a medial wall of the olfactory cleft, per one or more embodiments herein.

The observed jet column interacting with the medial and/or lateral wall to form a diverging thin sheet with defined edges may be due to the free jet column exiting the dispensing element tip impinging obliquely on the epithelial wall of the nasal cavity, as is shown in FIGS. 17B-17C. As shown, jet impingement may play a governing role in deposition characteristic formation based on the bounds of velocity and viscosity.

As is shown in FIGS. 17A-17D, a free jet column of fluid ejected obliquely from a dispensing element hits it target surface and spreads radially to form a circular sheet of fluid around the point of impact. A stagnation point is formed at the center of the sheet, where the velocity of the fluid is negligible, and a shear layer forms between the stagnant fluid and the surrounding fluid. The shear layer becomes unstable, leading to the formation of vortices that mix the fluid and create a recirculating rim region. A local surface pressure distribution from the jet's impingement can also form a thin boundary layer on the surface.

The three distinct deposition patterns formed by the impingement of a drug-containing formulation to specific regions or a combination of regions within the nasal cavity affects the diffusion/absorption of a formulation and resulting pharmacokinetics. Such deposition patterns are achieved without the need for specialized nozzles.

Example 1: Low Viscosity Fluid Delivery on Curved Glass Sheets

FIGS. 12A-12C illustrate ejection of a low viscosity fluid (1 cP) from a dispensing element as a continuous liquid stream striking a curved glass sheet at a velocity of about 1.54 m/s and forming a bolus deposition pattern. FIGS. 13A-13C illustrate ejection of a low viscosity fluid from a dispensing element as a continuous liquid stream striking a curved glass sheet at a velocity of about 3 m/s and forming a transitory deposition pattern. FIGS. 13D-13F illustrate ejection of a low viscosity fluid from a dispensing element as a continuous liquid stream striking a curved glass sheet at a velocity of about 5.6 m/s and forming a transitory deposition pattern. FIGS. 14A-14C illustrate ejection of a low viscosity fluid from a dispensing element as a continuous liquid stream striking a curved glass sheet at a velocity of about 7.6 m/s and forming a surface deposition pattern. FIGS. 14D-14F illustrate a low viscosity fluid striking a curved glass sheet at a velocity of about 11.5 m/s and forming a droplet deposition pattern. FIGS. 12A FIG. 12A shows an exemplary image of ejection of a low viscosity fluid from a dispensing element as a continuous liquid stream and hitting a curved glass sheet during bolus deposition at a velocity of 1.54 m/s. FIG. 12B shows an exemplary image of ejection of a low viscosity fluid from a dispensing element as a continuous liquid stream and at intermediate ejection during bolus deposition at a velocity of 1.54 m/s. FIG. 12C shows an exemplary image of ejection of a low viscosity fluid from a dispensing element as a continuous liquid stream and at final ejection during bolus deposition at a velocity of 1.54 m/s. As is shown in FIGS. 12A-12C, a bolus deposition may be ideal for deposition to the olfactory cleft and may allow for targeted deposition of a fluid to the olfactory cleft while minimizing off-target delivery.

Example 2: High Viscosity Fluid Delivery on Curved Glass Sheets

FIGS. 15A-15I show exemplary image of an increased 50 cP viscosity fluid ejected as a continuous liquid stream and hitting curved glass sheet. FIG. 15A shows an increased 50 cP viscosity fluid ejected as a continuous liquid stream and hitting curved glass sheet at a velocity of 5.78 m/s, resulting in a bolus deposition pattern. FIG. 15B shows an increased 50 cP viscosity fluid ejected as a continuous liquid stream and hitting curved glass sheet at intermediate ejection at a velocity of 5.78 m/s resulting in a bolus deposition pattern. FIG. 15C an increased 50 cP viscosity fluid ejected as a continuous liquid stream and hitting curved glass sheet at a final ejection at a velocity of 5.78 m/s resulting in a bolus deposition pattern. FIG. 15D an increased 50 cP viscosity fluid ejected as a continuous liquid stream and hitting curved glass sheet hitting a curved glass sheet at a velocity of 11.5 m/s resulting in a bolus deposition pattern. FIG. 15E shows an exemplary image an increased 50 cP viscosity fluid ejected as a continuous liquid stream and hitting curved glass sheet at an intermediate ejection at a velocity of 11.5 m/s resulting in a bolus deposition pattern. FIG. 15F shows an increased 50 cP viscosity fluid ejected as a continuous liquid stream and hitting curved glass sheet final ejection at a velocity of 11.5 m/s resulting in a bolus deposition pattern. FIG. 15G shows an increased 50 cP viscosity fluid ejected as a continuous liquid stream and hitting a curved glass sheet at a velocity of 13.27 m/s resulting in a bolus deposition pattern. FIG. 15H shows an exemplary image of intermediate ejection at a velocity of 13.27 m/s resulting in a bolus deposition pattern. FIG. 15I shows an increased 50 cP viscosity fluid ejected as a continuous liquid stream and hitting curved glass sheet a final ejection at a velocity of 13.27 m/s resulting in a bolus deposition pattern. As is shown in FIGS. 15A-15I, a bolus deposition may be ideal for deposition to the olfactory cleft and may allow for targeted deposition of a fluid to the olfactory cleft while minimizing off-target delivery. As is shown in FIGS. 15A-15I, a bolus deposition may be more easily achieved at across a wider range of velocities with an increased 50 cP viscosity fluid.

Example 3: Targeted Low Velocity Fluid Delivery to Olfactory Cleft

Figure 16A:
FIG. 16A illustrates an initial state of a low velocity fluid in a dispensing element in an exemplary nasal cavity model, per one or more embodiments herein.
Figure 16B:
FIG. 16B illustrates a sheet/rim formation state of a low velocity fluid following ejection from the dispensing element as it contacts a medial aspect of the olfactory cleft, per one or more embodiments herein.
Figure 16C:
FIG. 16C illustrates a recirculation state of a low velocity fluid following ejection from the dispensing element as it circulates about the olfactory cleft, per one or more embodiments herein.
Figure 16D:
FIG. 16D illustrates a final resting state in which a bolus deposition is formed by the low velocity fluid deposition on the olfactory cleft, per one or more embodiments herein.

FIG. 16A illustrates an initial state of fluid in a dispensing element in an exemplary nasal cavity model. FIG. 16B illustrates ejection of a 1 cP fluid from a dispensing element as a continuous liquid stream and forming a sheet/rim formation state of fluid deposition upon contacting a feature of the nasal anatomy, and movement towards an olfactory cleft. FIG. 16C illustrates a recirculation state of fluid following ejection of as a continuous liquid stream and recirculation state about an upper surface of the olfactory region before deposition on olfactory cleft. FIG. 16D illustrates the resulting bolus deposition pattern of the fluid on olfactory cleft, resulting in targeted delivery of the fluid to the olfactory cleft, and minimal delivery of the fluid to off-target regions.

Example 4: Targeted High Velocity Fluid Delivery to Olfactory Cleft

Figure 17D:
FIG. 17D illustrates a recirculation state of a high velocity fluid contacting a medial wall of the olfactory cleft in which a bolus deposition pattern is starting to form, per one or more embodiments herein.
Figure 17E:
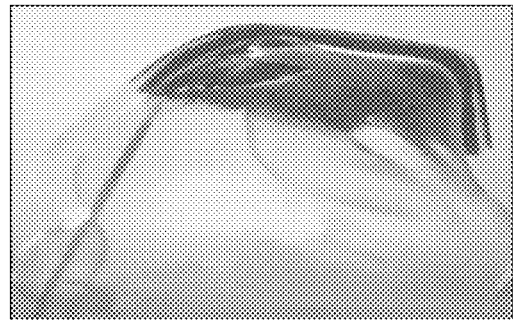
FIG. 17E illustrates a recirculation state of a high velocity fluid contacting a medial wall and an upper ridge of the olfactory cleft in which a bolus deposition pattern is forming, per one or more embodiments herein.
Figure 17F:
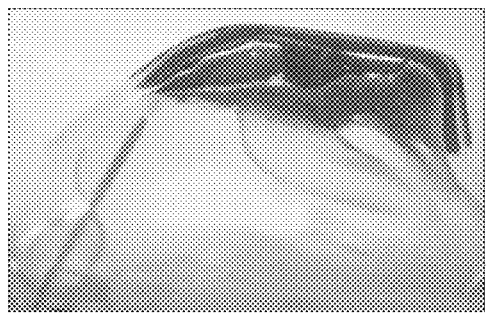
FIG. 17F illustrates a recirculation state of a high velocity fluid contacting a medial wall and an upper ridge of the olfactory cleft, per one or more embodiments herein.
Figure 17G:
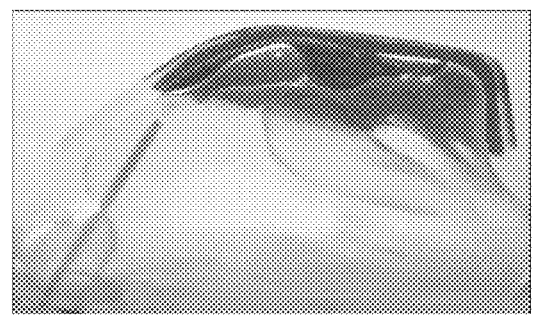
FIG. 17G illustrates a final resting state in which a bolus deposition is formed of a high velocity fluid deposition on the upper ridge and the medial walls olfactory cleft, per one or more embodiments herein.

FIG. 17A illustrates in a dispensing element in an exemplary nasal cavity model. FIG. 17B illustrates ejection of a 50 cP fluid from a dispensing element as a continuous liquid stream and forming a sheet/rim formation state of fluid deposition upon contacting a feature of the nasal anatomy, and movement towards an olfactory cleft. FIG. 17B illustrates a sheet/rim formation state of the fluid following ejection of as a continuous liquid stream and recirculation state about an upper surface of the olfactory region before deposition on olfactory cleft. FIG. 17C illustrates a sheet/rim formation state of the fluid following ejection of as a continuous liquid stream and recirculation state about an upper surface of the olfactory region before deposition on olfactory cleft. FIG. 17D illustrates a recirculation state of fluid following ejection of as a continuous liquid stream and recirculation state about an upper surface of the olfactory region before deposition on olfactory cleft. FIG. 17E illustrates a recirculation state of fluid following ejection of as a continuous liquid stream and recirculation state about an upper surface of the olfactory region before deposition on olfactory cleft. FIG. 17F illustrates a state of fluid coming to rest in the resulting bolus deposition pattern on olfactory cleft. FIG. 17G illustrates the resulting bolus deposition pattern of the fluid on olfactory cleft, resulting in targeted delivery of the fluid to the olfactory cleft, and minimal delivery of the fluid to off-target regions.

Definitions

Unless otherwise defined, all technical terms used herein have the same meaning as commonly understood by one of ordinary skill in the art to which this disclosure belongs.

As used herein, the singular forms "a," "an," and "the" include plural references unless the context clearly dictates otherwise. Any reference to "or" herein is intended to encompass "and/or" unless otherwise stated.

As used herein, the term "about" in some cases refers to an amount that is approximately the stated amount.

As used herein, the term "about" refers to an amount that is near the stated amount by 10%, 5%, or 1%, including increments therein.

As used herein, the term "about" in reference to a percentage refers to an amount that is greater or less the stated percentage by 10%, 5%, or 1%, including increments therein.

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "comprise", "comprising", or the like means additional elements or components other than those recited may be present. Other terms such as "include", "contain", "have" and the like have similar meaning.

The term "consist of", "consisting of" or the like means no additional component is present.

As used herein the term "composition" may include therapeutic compounds (small and large molecules), medicaments in liquid, powder, or gas form, or a combination thereof, or sampling fluids.

As used herein the term "dispensing element" comprises a dispensing element or a catheter, an insertable portion, a syringe, a fluid chamber, or a combination thereof, or anything that acts upon the dispensing element or the catheter, the syringe, or the fluid chamber.

As used herein the term "about" or "approximately" as used herein when referring to a measurable value such as a parameter, an amount, a temporal duration, and the like, is meant to encompass variations of +/−10% or less from the specified value, insofar such variations are appropriate to perform in the present disclosure. It is to be understood that the value to which the modifier "about" or "approximately" refers is itself also specifically disclosed.

As used herein the term "columella" is the firm tissue bridge that separates the nostrils at the base of the nose. The "columella" is the most anteroinferior portion of the nasal septum. The term "columella" or "columella region" is the subnasale, or an anterior nasale spine, or a combination thereof. The columella region may comprise a subnasale, or a combination thereof. The columella shape may be defined by an anterior nasal spine located posteriorly to the columella e.g., 1 cm.

As used herein the term "composition" or "compound" or "therapeutic" or "sampling compound" or "sampling fluid" is therapeutics, medicaments, drugs, small and large molecules, medicaments in liquid, powder, or gas form, or a combination thereof having a low, intermediate, or high viscosity.

As used herein the term "introduction pathway" is, in sequence, the vestibule, the anterior aspect of the internal nasal valve, and the anterior aspect of the respiratory region—anterior of the turbinates.

As used herein the term "internal nasal valve" (INV) is a space bounded medially by the dorsal septum 24 (or just septum), laterally by the caudal portion of the upper lateral cartilage, and inferiorly by the head of the inferior turbinate.

As used herein the term "nasal cavity" includes two nasal channels, each comprised of a vestibule, respiratory region and olfactory cleft, and a nasopharynx.

As used herein the term "turbinates" refers to superior turbinate, middle turbinate, or inferior turbinate, or a combination thereof.

As used herein the term "nasal cavity" refers to large, air-filled space behind the nose, where air passes on its way to the throat during inhalation.

As used herein the term "internal nasal valve" refers to narrowest part of the nasal airway, located just beyond the nostril. It's formed by the edge of the nasal septum, the upper lateral cartilage, and the floor of the nose. The internal nasal valve plays a critical role in regulating airflow through the nose. The area of interest is superior (above) to this structure.

As used herein the term "nasal septum" refers to bone and cartilage that separates the right and left nostrils. It forms the medial (towards the middle) boundary of the region of interest.

As used herein the term "lateral nasal wall" refers to the side wall of the nasal cavity, which is opposite to the nasal septum. It's a complex structure that includes the turbinates (long, curled bones that protrude into the nasal cavity) and the meatuses (grooves or channels between the turbinates). The lateral nasal wall forms the lateral (towards the side) boundary of the region of interest.

As used herein the term "middle and superior meatuses" refers to spaces within the nasal cavity located between the turbinates. The middle meatus is located beneath the middle turbinate and above the inferior turbinate, and the superior meatus is located beneath the superior turbinate. The region of interest encompasses parts of these spaces.

As used herein the term "nostril" refers to the two openings of the nose where air enters.

As used herein the term "nasal vestibule" refers to the most anterior part of the nasal cavity, just inside the nostrils. It's the area of the nose that protrudes outside the face predominantly. This area is lined with skin and contains hair follicles, and it acts as the initial filtering and warming area for inhaled air before it moves deeper into the nasal cavity. The nasal vestibule extends posteriorly to the nasal valve, which is the narrowest part of the nasal airway and located just beyond the nostril.

As used herein the term "turbinates" refers to three pairs of bony projections (inferior, middle, and superior) covered in mucous membrane that protrude into the nasal cavity from the lateral walls. They increase the surface area of the nasal cavity, aiding in the warming, humidification, and filtration of inhaled air.

As used herein the term "meatuses" refers to the spaces located between the turbinates. Each turbinate has a corresponding meatus underneath it (i.e., inferior, middle, and superior meatus).

As used herein the term "olfactory region" refers to a small area located at the top of the nasal cavity, where the sense of smell is located.

ENUMERATED EMBODIMENTS

Enumerated embodiment 1. A method of delivering a fluid having a viscosity of less than about 3000 centipoise (cP) to a targeted sub-region of a subject's nasal cavity, the method comprising:
  (a) ejecting a discrete volume of the fluid as a continuous stream from a dispensing element of a device;
  (b) moving the continuous stream through an airspace in the nasal cavity towards the targeted sub-region;
  (c) contacting an anatomical feature of the subject's nasal cavity with the continuous stream and forcing the fluid to move around the anatomical feature and towards the targeted sub-region; and
  (d) contacting the targeted sub-region of the subject's nasal cavity with the fluid, thereby delivering the fluid to the targeted sub-region of the subject's nasal cavity.

Enumerated embodiment 2. The method of any one of the enumerated embodiments, wherein the viscosity of the fluid is less than about 2500 cP.

Enumerated embodiment 3. The method of any one of the enumerated embodiments, wherein the viscosity of the fluid is less than about 2000 cP.

Enumerated embodiment 4. The method of any one of the enumerated embodiments, wherein the viscosity of the fluid is less than about 1500 cP.

Enumerated embodiment 5. The method of any one of the enumerated embodiments, wherein the viscosity of the fluid is less than about 1000 cP.

Enumerated embodiment 6. The method of any one of the enumerated embodiments, wherein the viscosity of the fluid is less than about 500 cP.

Enumerated embodiment 7. The method of any one of the enumerated embodiments, wherein the viscosity of the fluid is less than about 250 cP.

Enumerated embodiment 8. The method of any one of the enumerated embodiments, wherein the viscosity of the fluid is less than about 100 cP.

Enumerated embodiment 9. The method of any one of the enumerated embodiments, wherein the viscosity of the fluid is less than about 50 cP.

Enumerated embodiment 10. The method of any one of the enumerated embodiments, wherein at a distance of 5 mm from the dispensing tip, a flux through a planar surface orthogonal to a flow path of the continuous stream possesses a gas component by volume not exceeding about 35%.

Enumerated embodiment 11. The method of any one of the enumerated embodiments, wherein the gas component by volume does not exceed about 20%.

Enumerated embodiment 12. The method of any one of the enumerated embodiments, wherein the ejecting the continuous stream of the fluid from the dispensing element results in a change in a velocity of the fluid of less than about 25%, when measured from a first point before ejection from the dispensing element to a second point 5 mm after ejection from the dispensing element, and wherein optionally, the first point before ejection from the dispensing element is within the dispensing element and is no greater than 3 mm from the point of ejection.

Enumerated embodiment 13. The method of any one of the enumerated embodiments, wherein the change in the velocity of the fluid is less than about 10%.

Enumerated embodiment 14. The method of any one of the enumerated embodiments, wherein the method does not result in substantial deposition of the fluid in a region of the subject's nasal cavity, which is not the targeted sub-region, immediately following the contacting of step (d).

Enumerated embodiment 15. The method of any one of the enumerated embodiments, wherein the method results in less than about 10%, about 5%, about 1%, about 0.1%, or about 0.01% of the fluid being deposited in a region of the subject's nasal cavity, which is not the targeted sub-region, immediately following the contacting of step (d).

Enumerated embodiment 16. The method of any one of the enumerated embodiments, wherein forcing the fluid to move around the anatomical feature comprises changing a direction of movement of the fluid relative to a direction of movement of the fluid in (b).

Enumerated embodiment 17. The method of any one of the enumerated embodiments, wherein at a distance of 5 mm from the dispensing tip, a flux through a planar surface orthogonal to a flow path of the continuous stream possesses a gas component by volume not exceeding about 20%.

Enumerated embodiment 18. The method of any one of the enumerated embodiments, wherein at a distance of 5 mm from the dispensing tip, the flux through a planar surface orthogonal to a flow path of the continuous stream possesses a gas component by volume not exceeding about 10%.

Enumerated embodiment 19. The method of any one of the enumerated embodiments, wherein at a distance of 5 mm from the dispensing tip, the flux through a planar surface orthogonal to a flow path of the continuous stream possesses a gas component by volume not exceeding about 5%.

Enumerated embodiment 20. The method of any one of the enumerated embodiments, wherein at a distance of 5 mm from the dispensing tip, the flux through a planar surface orthogonal to a flow path of the continuous stream possesses a gas component by volume not exceeding about 1%.

Enumerated embodiment 21. The method of any one of the enumerated embodiments, wherein the ejecting the continuous stream of the fluid from the dispensing elements change a velocity of the fluid by less than about 5%.

Enumerated embodiment 22. The method of any one of the enumerated embodiments, wherein the ejecting the discrete volume of the fluid as the continuous stream ejects the continuous stream in a velocity vector of the continuous stream which has a vorticity of less than about 0.2× the magnitude of the velocity vector at the time of the ejecting from the dispensing element.

Enumerated embodiment 23. The method of any one of the enumerated embodiments, wherein the moving the continuous stream through the airspace in the nasal cavity occurs along a velocity vector of the continuous stream which has a vorticity of less than about 0.2× the magnitude of the velocity vector at the time of the ejecting from the dispensing element.

Enumerated embodiment 24. The method of any one of the enumerated embodiments, wherein the continuous stream is ejected in a non-rotating vector.

Enumerated embodiment 25. The method of any one of the enumerated embodiments, wherein the contacting the targeted sub-region of the subject's nasal cavity comprises depositing the fluid onto the targeted sub-region in a bolus deposition pattern, immediately following the contacting of step (d).

Enumerated embodiment 26. The method of any one of the enumerated embodiments, wherein the bolus deposition pattern comprises deposition of the continuous stream onto the targeted sub-region in a cohesive liquid mass.

Enumerated embodiment 27. The method of any one of the enumerated embodiments, wherein the cohesive liquid mass comprises at least about 75% of the fluid ejected from the dispensing element.

Enumerated embodiment 28. The method of any one of the enumerated embodiments, wherein the bolus deposition pattern comprises deposition of the continuous stream onto the targeted sub-region without substantial formation of droplets, immediately following the contacting of step (d).

Enumerated embodiment 29. The method of any one of the enumerated embodiments, wherein less than about 15%, about 10%, about 5%, about 1%, about 0.1%, or about 0.01% of the fluid ejected from the dispensing element forms droplets.

Enumerated embodiment 30. The method of any one of the enumerated embodiments, wherein the ejecting the continuous stream of the fluid from the dispensing element occurs at a velocity of about 1.5 m/s to about 3 m/s.

Enumerated embodiment 31. The method of any one of the enumerated embodiments, wherein the viscosity of the fluid is about 1 cP.

Enumerated embodiment 32. The method of any one of the enumerated embodiments, wherein the viscosity of the fluid is about 1 cP to about 10 cP.

Enumerated embodiment 33. The method of any one of the enumerated embodiments, wherein the ejecting the continuous stream of the fluid from the dispensing element occurs at a velocity of up to about 20 m/s.

Enumerated embodiment 34. The method of any one of the enumerated embodiments, wherein the ejecting the continuous stream of the fluid from the dispensing element occurs at a velocity of about 5 m/s to about 15 m/s.

Enumerated embodiment 35. The method of any one of the enumerated embodiments, wherein the viscosity of the fluid is at least about 10 cP.

Enumerated embodiment 36. The method of any one of the enumerated embodiments, wherein the viscosity of the fluid is about 10 cP to about 100 cP.

Enumerated embodiment 37. The method of any one of the enumerated embodiments, wherein the viscosity of the fluid is about 25 cP to about 75 cP.

Enumerated embodiment 38. The method of any one of the enumerated embodiments, wherein the viscosity of the fluid is about 50 cP.

Enumerated embodiment 39. The method of any one of the enumerated embodiments, wherein ejecting the continuous stream of the fluid from the dispensing element results in the formation of a liquid chain fluid profile or a semi-closed rim fluid profile upon the contacting of step (c).

Enumerated embodiment 40. The method of any one of the enumerated embodiments, wherein the contacting the targeted sub-region of the subject's nasal cavity comprises depositing the fluid onto the targeted sub-region in a surface deposition pattern, immediately following the contacting of step (d).

Enumerated embodiment 41. The method of any one of the enumerated embodiments, wherein the surface deposition pattern comprises deposition of the continuous stream onto the targeted sub-region in a liquid sheet.

Enumerated embodiment 42. The method of any one of the enumerated embodiments, wherein the liquid sheet comprises substantially no droplets.

Enumerated embodiment 43. The method of any one of the enumerated embodiments, wherein the liquid sheet comprises less than about 10%, about 5%, about 1%, about 0.1%, or about 0.01% of the fluid ejected forming droplets.

Enumerated embodiment 44. The method of any one of the enumerated embodiments, wherein the droplets comprise a diameter of about 120 micrometers to about 0.5 millimeters.

Enumerated embodiment 45. The method of any one of the enumerated embodiments, wherein the surface deposition pattern comprises deposition of the continuous stream onto the targeted sub-region in a plurality of droplets with a diameter of more than about 120 micrometers.

Enumerated embodiment 46. The method of any one of the enumerated embodiments, wherein the ejecting the continuous stream of the fluid from the dispensing element occurs at a velocity of about 3 m/s to about 11 m/s.

Enumerated embodiment 47. The method of any one of the enumerated embodiments, wherein the ejecting the continuous stream of the fluid from the dispensing element occurs at a velocity of about 7 m/s to about 11 m/s.

Enumerated embodiment 48. The method of any one of the enumerated embodiments, wherein the viscosity of the fluid is about 1 cP.

Enumerated embodiment 49. The method of any one of the enumerated embodiments, wherein the viscosity of the fluid is about 1 cP to about 10 cP.

Enumerated embodiment 50. The method of any one of the enumerated embodiments, wherein ejecting the continuous stream of the fluid from the dispensing element results in the formation of a liquid rim fluid profile upon the contacting of step (c).

Enumerated embodiment 51. The method of any one of the enumerated embodiments, wherein the liquid rim fluid profile comprises a semi-closed rim fluid profile, an open rim fluid profile, or an unstable rim fluid profile.

Enumerated embodiment 52. The method of any one of the enumerated embodiments, wherein the contacting the targeted sub-region of the subject's nasal cavity comprises depositing the fluid onto the targeted sub-region in a droplet deposition pattern, immediately following the contacting of step (d).

Enumerated embodiment 53. The method of any one of the enumerated embodiments, wherein the droplet deposition pattern comprises deposition of the continuous stream onto the targeted sub-region in a plurality of droplets with a diameter of about 120 micrometers to about 0.5 millimeters.

Enumerated embodiment 54. The method of any one of the enumerated embodiments, wherein the ejecting the continuous stream of the fluid from the dispensing element occurs at a velocity of at least about 11 m/s.

Enumerated embodiment 55. The method of any one of the enumerated embodiments, wherein the viscosity of the fluid is about 1 cP.

Enumerated embodiment 56. The method of any one of the enumerated embodiments, wherein the viscosity of the fluid is about 1 cP to about 10 cP.

Enumerated embodiment 57. The method of any one of the enumerated embodiments, wherein ejecting the continuous stream of the fluid from the dispensing element results in the formation of an impact wave fluid profile upon the contacting of step (c).

Enumerated embodiment 58. The method of any one of the enumerated embodiments, wherein the targeted sub-region is an olfactory cleft.

Enumerated embodiment 59. The method of any one of the enumerated embodiments, wherein the contacting the olfactory cleft comprises coating a surface of the olfactory cleft.

Enumerated embodiment 60. The method of any one of the enumerated embodiments, wherein the contacting the olfactory cleft comprises partially filling a volume of the nasal cavity comprising the olfactory cleft.

Enumerated embodiment 61. The method of any one of the enumerated embodiments, wherein a capillary bridge is formed by the fluid, wherein the capillary bridge contacts opposing sides of an olfactory region of the subject's nasal cavity, and supports a coating of the fluid about the olfactory cleft.

Enumerated embodiment 62. The method of any one of the enumerated embodiments, wherein the targeted sub-region is an olfactory cleft.

Enumerated embodiment 63. The method of any one of the enumerated embodiments, wherein the targeted sub-region is a middle turbinate.

Enumerated embodiment 64. The method of any one of the enumerated embodiments 3, wherein the contacting the middle turbinate comprises coating a surface of the middle turbinate.

Enumerated embodiment 65. The method of any one of the enumerated embodiments, wherein the contacting the middle turbinate partially filling a volume of the nasal cavity comprising the middle turbinate.

Enumerated embodiment 66. The method of any one of the enumerated embodiments, wherein the targeted sub-region is a middle turbinate.

Enumerated embodiment 67. The method of any one of the enumerated embodiments, wherein moving the continuous stream through the airspace in the nasal cavity comprises the continuous stream traveling at least about 0.2 cm through the airspace before contacting the targeted subregion.

Enumerated embodiment 68. The method of any one of the enumerated embodiments, wherein the targeted subregion is an olfactory cleft of the subject, and wherein substantially none of the fluid is deposited outside of the olfactory cleft of the subject, immediately following the contacting of step (d).

Enumerated embodiment 69. The method of any one of the enumerated embodiments, wherein the targeted subregion is an olfactory cleft of the subject, and wherein less than about 10% vol. of the fluid is deposited outside of the olfactory cleft of the subject, immediately following the contacting of step (d).

Enumerated embodiment 70. The method of any one of the enumerated embodiments, wherein the targeted subregion is a middle turbinate of the subject, and wherein substantially none of the fluid is deposited outside the middle turbinate of the subject, immediately following the contacting of step (d).

Enumerated embodiment 71. The method of any one of the enumerated embodiments, wherein the targeted subregion is a middle turbinate of the subject, and wherein less than about 10%, about 5%, about 1%, about 0.1%, or about 0.01% of the fluid is deposited outside the middle turbinate of the subject, immediately following the contacting of step (d).

Enumerated embodiment 72. The method of any one of the enumerated embodiments, wherein the ejecting the bolus of the fluid from the dispensing element occurs with a Reynolds number of less than about 2,000 measured at the point of ejection from the dispensing element.

Enumerated embodiment 73. The method of any one of the enumerated embodiments, wherein the ejecting the bolus of the fluid from the dispensing element occurs with a Reynolds number of less than about 500 measured at the point of ejection from the dispensing element.

Enumerated embodiment 74. The method of any one of the enumerated embodiments, wherein the discrete volume of the fluid comprises a volume of up to about 200 μL.

Enumerated embodiment 75. The method of any one of the enumerated embodiments, wherein the discrete volume of the fluid comprises a volume of about 100 μL.

Enumerated embodiment 76. The method of any one of the enumerated embodiments, wherein the discrete volume of the fluid comprises a volume of 50-200 μL.

Enumerated embodiment 77. The method of any one of the enumerated embodiments, wherein the dispensing element comprises an unobstructed opening at the tip of the dispensing element.

Enumerated embodiment 78. The method of any one of the enumerated embodiments, wherein the dispensing element does not comprise an atomizer.

Enumerated embodiment 79. The method of any one of the enumerated embodiments, wherein the anatomical feature of the subject's nasal cavity is a septum.

Enumerated embodiment 80. The method of any one of the enumerated embodiments, wherein a diameter of the continuous stream is about 1-10 mm upon the ejecting from the dispensing element.

Enumerated embodiment 81. The method of any one of the enumerated embodiments, wherein a diameter of the continuous stream is about 3-6 mm upon the ejecting from the dispensing element.

Enumerated embodiment 82. The method of any one of the enumerated embodiments, wherein the fluid comprises a medicament.

Enumerated embodiment 83. The method of any one of the enumerated embodiments, wherein the medicament comprises a biologic, a protein, a nucleic acid, a vaccine, or a large molecule drug.

Enumerated embodiment 84. The method of any one of the enumerated embodiments, wherein the medicament comprises a small molecule drug.

Enumerated embodiment 85. The method of any one of the enumerated embodiments, wherein the ejecting of the discrete volume of the fluid occurs at a velocity of up to 50 m/s.

Enumerated embodiment 86. The method of any one of the enumerated embodiments, wherein the targeted sub-region is a superior turbinate.

Enumerated embodiment 87. The method of any one of the enumerated embodiments, wherein the targeted sub-region is a middle turbinate or a superior turbinate.

All publications, patents, and patent applications mentioned in this specification are herein incorporated by reference to the same extent as if each individual publication, patent, or patent application was specifically and individually indicated to be incorporated by reference.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the present disclosure may be employed in practicing the present disclosure. It is intended that the following claims define the scope of the present disclosure and that methods and devices within the scope of these claims and their equivalents be covered thereby.

What is claimed is:

1. A method of delivering a fluid having a viscosity of less than about 3000 centipoise (cP) to a targeted sub-region of a subject's nasal cavity, the method comprising:

(a) ejecting a discrete volume of the fluid as a continuous stream from a dispensing element of a device;

(b) moving the continuous stream through an airspace in the nasal cavity towards the targeted sub-region;

(c) contacting an anatomical feature of the subject's nasal cavity with the continuous stream and forcing the fluid to move around the anatomical feature and towards the targeted sub-region; and (d) contacting the targeted sub-region of the subject's nasal cavity with the fluid, thereby delivering the fluid to the targeted sub-region of the subject's nasal cavity wherein the contacting the targeted sub-region of the subject's nasal cavity comprises depositing the fluid onto the targeted sub-region in a bolus deposition pattern, immediately following the contacting of step (d);

wherein the bolus deposition pattern comprises deposition of the continuous stream onto the targeted sub-region without substantial formation of droplets, immediately following the contacting of step (d).

2. The method of claim 1, wherein at a distance of 5 mm from the dispensing tip, a flux through a planar surface orthogonal to a flow path of the continuous stream possesses a gas component by volume not exceeding about 35%.

3. The method of claim 1, wherein the ejecting the continuous stream of the fluid from the dispensing element results in a change in a velocity of the fluid of less than about 25%, when measured from a first point before ejection from the dispensing element to a second point 5 mm after ejection from the dispensing element, and wherein optionally, the first point before ejection from the dispensing element is within the dispensing element and is no greater than 3 mm from the point of ejection.

4. The method of claim 1, wherein the method does not result in substantial deposition of the fluid in a region of the subject's nasal cavity, which is not the targeted sub-region, immediately following the contacting of step (d).

5. The method of claim 1, wherein the method results in less than about 10%, about 5%, about 1%, about 0.1%, or about 0.01% of the fluid being deposited in a region of the subject's nasal cavity, which is not the targeted sub-region, immediately following the contacting of step (d).

6. The method of claim 1, wherein forcing the fluid to move around the anatomical feature comprises changing a direction of movement of the fluid relative to a direction of movement of the fluid in (b).

7. The method claim 1, wherein at a distance of 5 mm from the dispensing tip, a flux through a planar surface orthogonal to a flow path of the continuous stream possesses a gas component by volume not exceeding about 20%.

8. The method of claim 1, wherein the ejecting the continuous stream of the fluid from the dispensing elements change a velocity of the fluid by less than about 5%.

9. The method of claim 1, wherein the ejecting the discrete volume of the fluid as the continuous stream ejects the continuous stream in a velocity vector of the continuous stream which has a vorticity of less than about 0.2× the magnitude of the velocity vector at the time of the ejecting from the dispensing element.

10. The method of claim 1, wherein the moving the continuous stream through the airspace in the nasal cavity occurs along a velocity vector of the continuous stream which has a vorticity of less than about 0.2× the magnitude of the velocity vector at the time of the ejecting from the dispensing element.

11. The method of claim 1, wherein the continuous stream is ejected in a non-rotating vector.

12. The method of claim 1, wherein the bolus deposition pattern comprises deposition of the continuous stream onto the targeted sub-region in a cohesive liquid mass.

13. The method of claim 12, wherein the cohesive liquid mass comprises at least about 75% of the fluid ejected from the dispensing element.

14. The method of claim 1, wherein less than about 15%, about 10%, about 5%, about 1%, about 0.1%, or about 0.01% of the fluid ejected from the dispensing element forms droplets.

15. The method of claim 1, wherein the contacting the targeted sub-region of the subject's nasal cavity comprises depositing the fluid onto the targeted sub-region in a surface deposition pattern, immediately following the contacting of step (d).

16. The method of claim 1, wherein the targeted sub-region is an olfactory cleft.

17. The method of claim 1, wherein the targeted sub-region is a middle turbinate or a superior turbinate.

18. The method of claim 1, wherein the anatomical feature of the subject's nasal cavity is a septum.

19. The method of claim 1, wherein a diameter of the continuous stream is about 1-10 mm upon the ejecting from the dispensing element.

20. The method of claim 1, wherein the ejecting of the discrete volume of the fluid occurs at a velocity of up to 50 m/s.

* * * * *